(12) United States Patent
Wu et al.

(10) Patent No.: US 8,580,763 B2
(45) Date of Patent: *Nov. 12, 2013

(54) 2, 6-DINITROGEN-CONTAINING SUBSTITUTED PURINE DERIVATIVES, THE PREPARATION AND USES THEREOF

(75) Inventors: Zhanggui Wu, Hangzhou (CN);
Weidong Ye, Xinchang County (CN);
Jianyong Yuan, Xinchang County (CN);
Gang Chen, Xinchang County (CN)

(73) Assignees: Zhanggui Wu, Hangzhou (CN); Zhe Jiang Medicine Co., Ltd, Chengguan Town (CN)

( * ) Notice: Subject to any disclaimer, the term of this patent is extended or adjusted under 35 U.S.C. 154(b) by 611 days.

This patent is subject to a terminal disclaimer.

(21) Appl. No.: 12/596,669

(22) PCT Filed: Apr. 17, 2008

(86) PCT No.: PCT/CN2008/000782
§ 371 (c)(1),
(2), (4) Date: Feb. 18, 2010

(87) PCT Pub. No.: WO2008/128428
PCT Pub. Date: Oct. 30, 2008

(65) Prior Publication Data
US 2010/0144663 A1    Jun. 10, 2010

(30) Foreign Application Priority Data
Apr. 20, 2007    (CN) .......................... 2007 1 0039725

(51) Int. Cl.
*A01N 43/04*    (2006.01)
*A61K 31/70*    (2006.01)

(52) U.S. Cl.
USPC .................. 514/48; 514/43; 514/45; 514/46; 514/47; 536/27.1; 536/27.13

(58) Field of Classification Search
None
See application file for complete search history.

(56) References Cited

U.S. PATENT DOCUMENTS 7,399,754 B2 *    7/2008    Wu .................................. 514/48

OTHER PUBLICATIONS

Bubenik et al. Bioorganic & Medicinal Chemistry Letters 12 (2002) 3063-3066.*

* cited by examiner

*Primary Examiner* — Patrick Lewis
(74) *Attorney, Agent, or Firm* — William D. Hare; McNeely, Hare & War LLP

(57) ABSTRACT

The present invention provides 2,6-dinitrogen-containing substituted purine compounds of formula (A) or salts or solvates thereof or the solvates of salts thereof, as well as pharmaceutical compositions containing such compounds. The compounds of the present invention have the characteristics of lower toxicity, broad anticancer spectrum, higher anticancer activity, good stability and the like. The compounds are useful for the manufacture of an antitumor medicament. The present invention also provides a process for preparing these compounds.

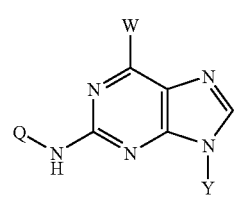

A

18 Claims, No Drawings

2,6-DINITROGEN-CONTAINING SUBSTITUTED PURINE DERIVATIVES, THE PREPARATION AND USES THEREOF

FIELD OF THE INVENTION

The present invention relates to pharmaceutical chemistry, specifically relates to 2,6-dinitrogen-containing substituted purine derivatives, method for preparing the same and the use thereof.

BACKGROUND OF THE INVENTION

Malignant tumor (cancer) is one of the main diseases to seriously influence human health and threaten human life currently. More than 5 million people die of cancer all over the world every year. Even though there already have some therapeutic means such as surgery, radiotherapy, chemotherapy or the like, their cure rate is generally not high. At present, the chemotherapy mainly exsits some deficiencies such as poor selectivity, severe side effect and the like. Thus it is becoming one of the working focus of pharmacy operator every country to find antitumor medicament having lower toxicity, mild side effect, higher anticancer activity, good stability, etc.

It is reported that some purine derivatives have certain antiviral and antitumor activities. Please refer to relevant reports of EP 0353955, WO 9201968, JP10120682, KR9100441, etc.

Some substituted purine derivatives also are disclosed in prior art, for example, $N^6$-disubstituted purin derivatives used for treating allergic diseases are disclosed in U.S. Pat. No. 4,853,386; 6-cyclopropylamino-9H-purine derivatives having antiviral activity are disclosed in JP2003-55377A and JP 2003-119197A. Glycosylated purin derivatives having anti-inflammatory effects are disclosed in J. Org. Chem. (pages 3212~3215. vol. 69, 2004). $N^2$-butylphenyl-2'-deoxy purin derivatives having activities of DNA α polymerase of eukaryotic cells are disclosed in J. Med. Chem. (pages 175~181, vol. 27, 1984). 2,6,9-trisubstituted purin derivatives are disclosed in Tetrahedron Letters (1827~1830, vol. 39, 1998). Further some compounds having antitumor effects are disclosed in the patent CN200510026846. It is a worthy attention to people to design $N^2,N^6$-disubstituted purin derivatives having better antitumor activity in further researches for filtering of antitumor activity of $N^2,N^6$-disubstituted purin compound.

SUMMARY OF THE INVENTION

The technical problem of the present invention lies in researches for designing $N^2,N^6$-disubstituted purin derivatives having lower toxicity, broad anticancer spectrum, higher anticancer activity, good stability.

The present invention provides 2,6-dinitrogen-containing substituted purine compounds of formula (A) or salts or solvates thereof or the solvates of salts thereof:

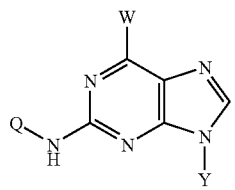

A

Wherein W represents an optionally monosubstituted $C_1$~$C_6$ straight or branched alkylamino, an optionally mono-substituted $C_3$~$C_6$ straight or branched alkyl or alkenyl or alkynyl amino, an optionally disubstituted $C_1$~$C_6$ straight or branched alkylamino, an optionally disubstituted $C_3$~$C_6$ straight or branched alkyl or alkenyl or alkynyl amino, W may also represent amino substituted by two different $C_1$~$C_6$ straight or branched alkane, or represent amino substituted by two different $C_3$~$C_6$ straight or branched olefin, or amino which one end is substituted by $C_1$~$C_6$ alkane and the other end is substituted by $C_3$~$C_6$ olefin, or an optionally substituted heterocycle containing secondary nitrogen, such as pyrrolidine, piperidine, morphine or piperazidine; the substituent represents $C_1$~$C_6$ straight or branched alkyl or halogen or hydroxyl;

Y represents H or a pharmaceutically acceptable saccharide, wherein the saccharide represents preferably any one of the following formulas:

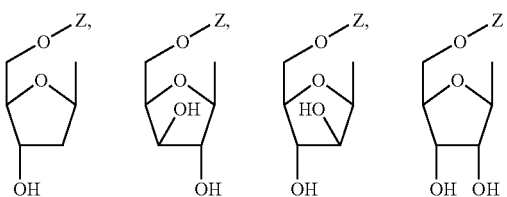

Z represents H or any one of the following formulas:

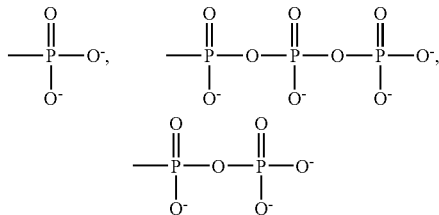

Q represents H or any one of the following formulas:

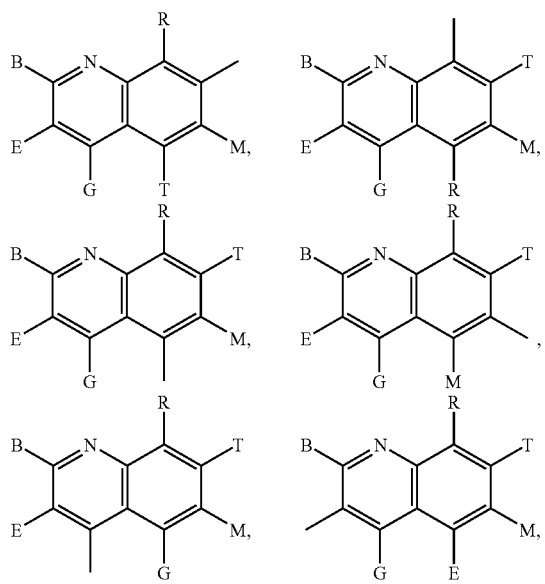

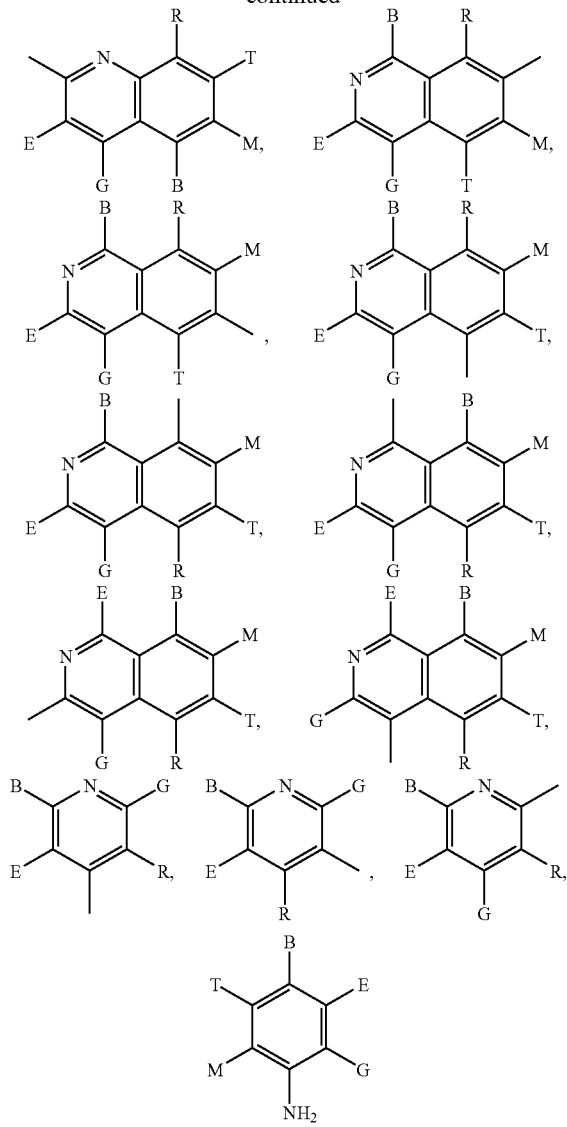

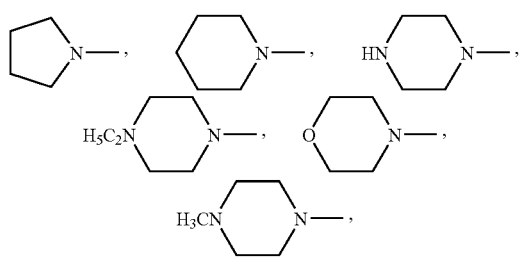

Wherein B, E, G, R, T, M each independently represents a H or a $C_1$~$C_6$ straight or branched alkyl, or haloalkyl, a $C_3$~$C_6$ cycloalkyl, halogen, CN, $NH_2$, methoxyl, ethyoxyl or nitro.

Preferably, W represents amino, cyclopropylamino, cyclobutylamino, methylamino, ethylamino, propylamino, isopropylamino, dimethylamino, diethylamino, methylethylamino, allylamino, methylallylamino, ethylallylamino, propylallylamino, diallylamino, ethanolamino or any one of the following formulas:

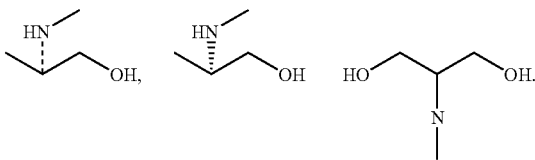

Preferably, W represents cyclopropylamino, dimethylamino, diethylamino, methylethylamino, allylamino, diallylamino or any one of the following formulas:

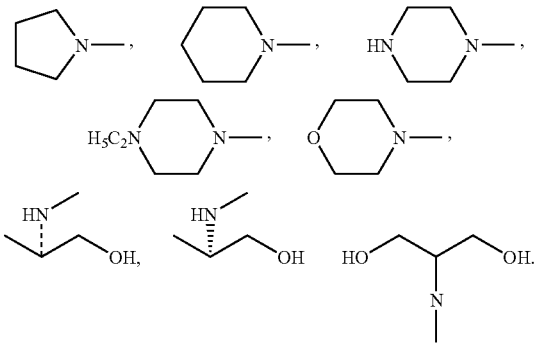

Q preferably represents any one of the following formulas:

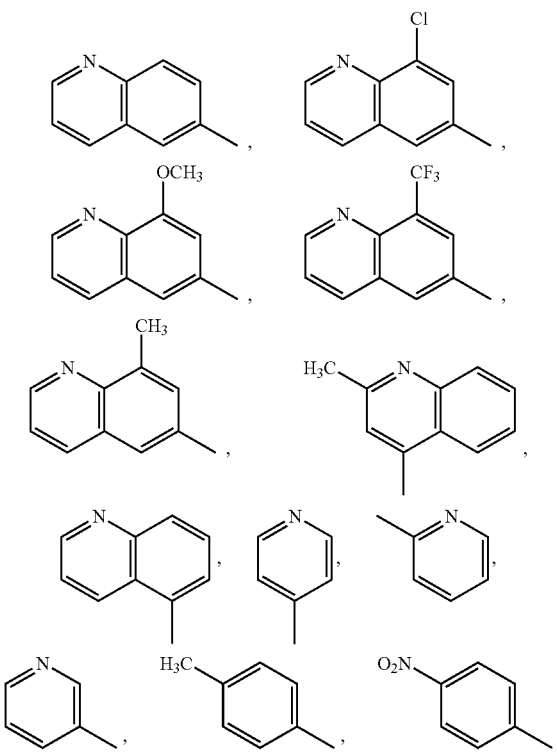

Wherein Y is H.

The present invention particularly provides the following compounds:
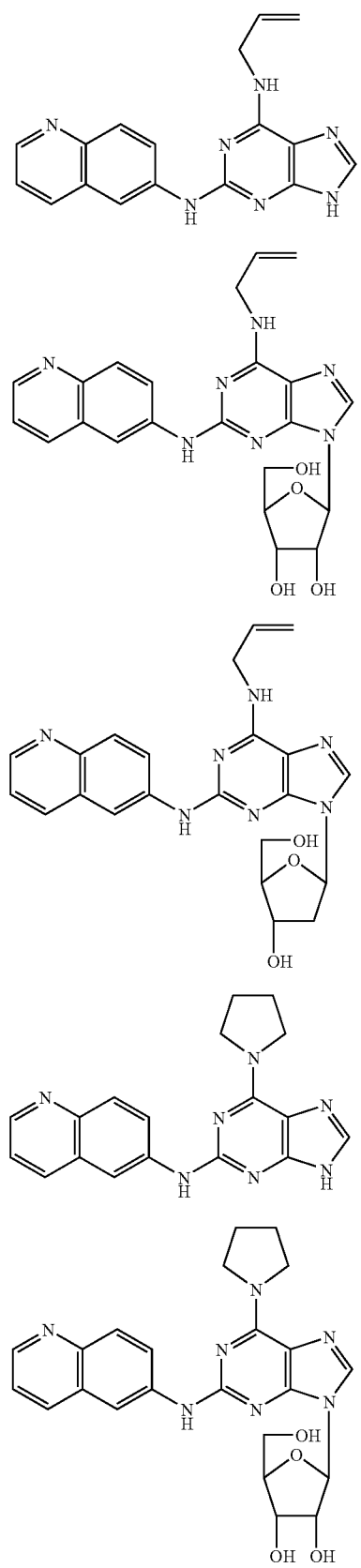
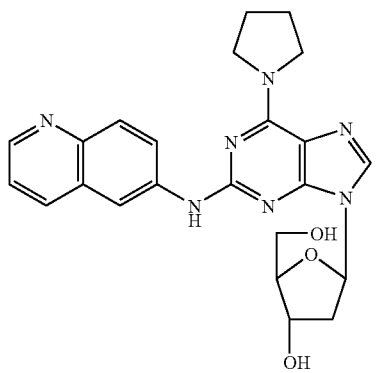
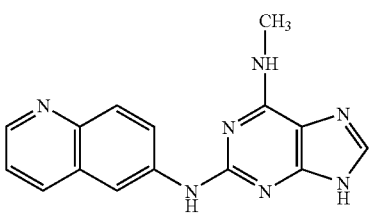
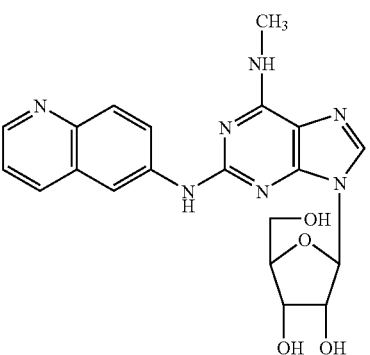
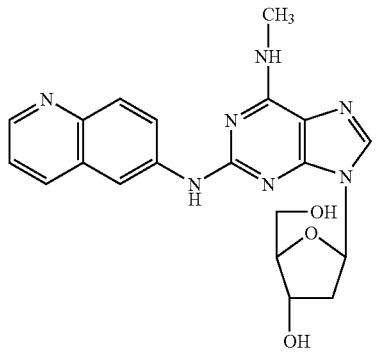
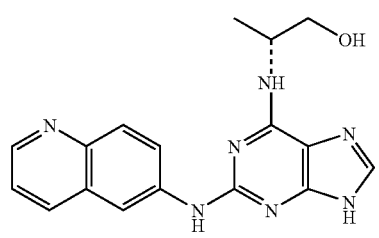

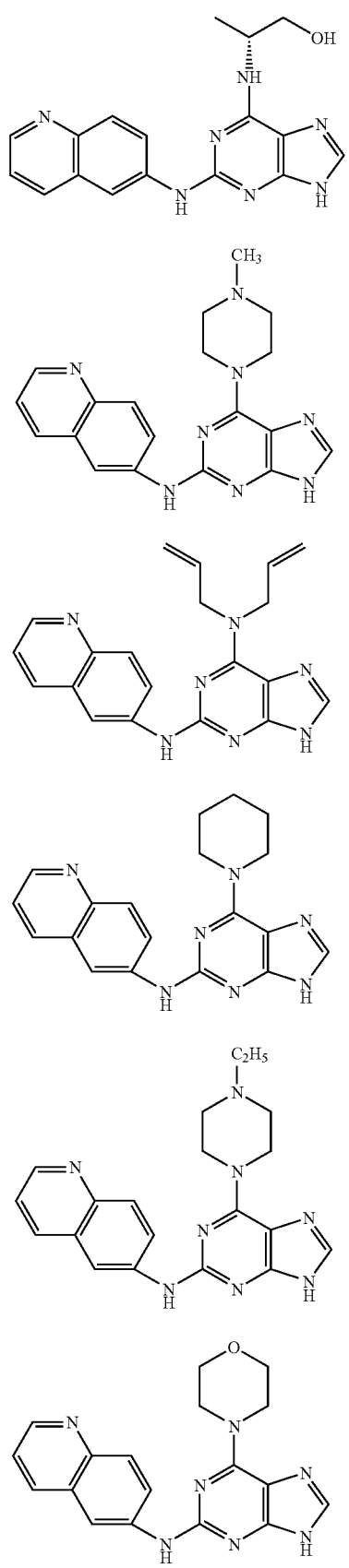
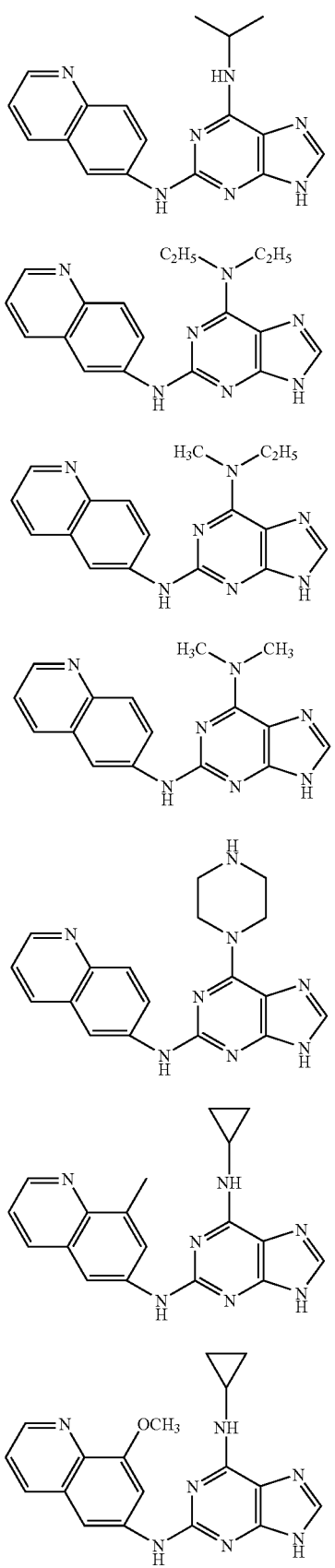

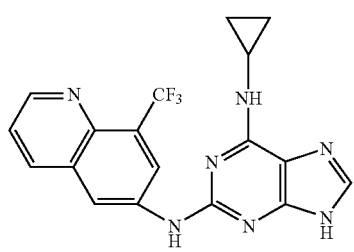
XXIV
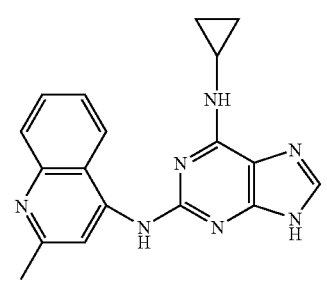
XXV
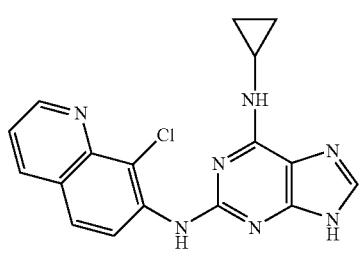
XXVI
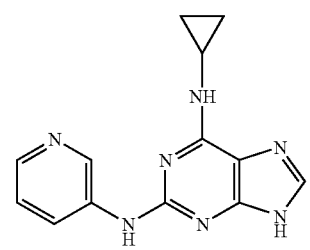
XXVII
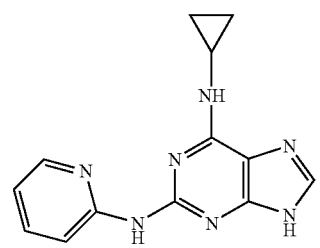
XXVIII
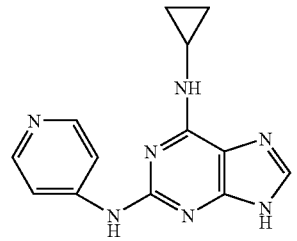
XXIX
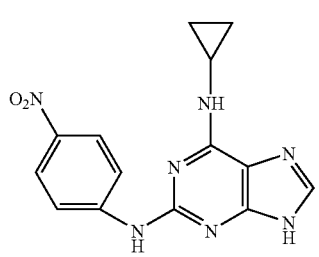
XXX
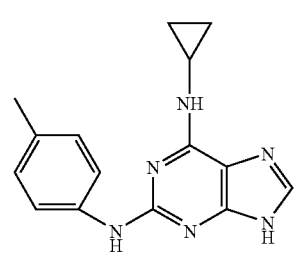
XXXI
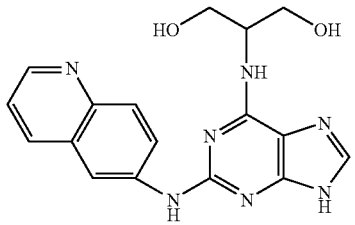
XXXII
It is another object of the present invention to provide a method for preparing the above compounds of formula (A) or salts or solvates thereof or solvates of salts thereof, and the method is shown in the following formula:
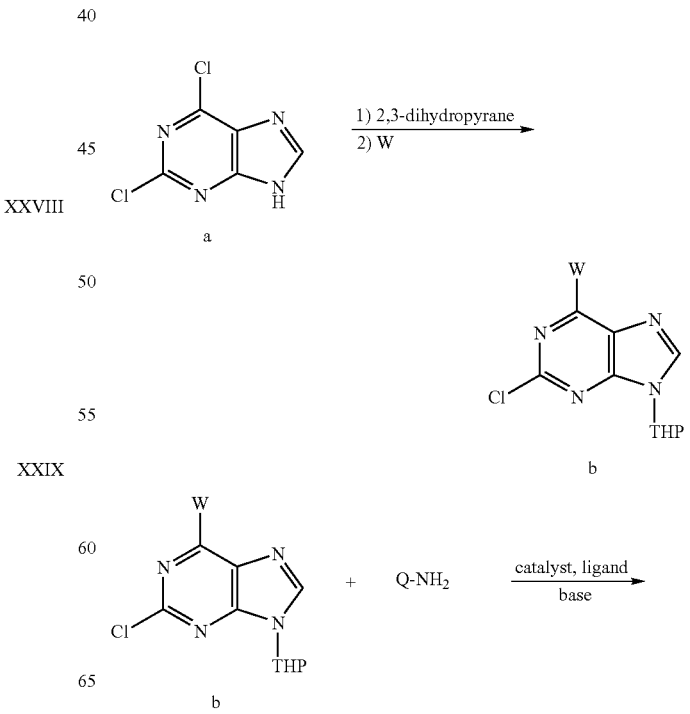

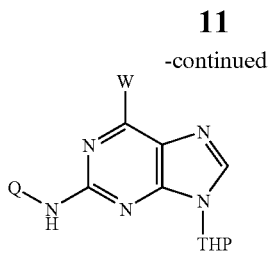

c

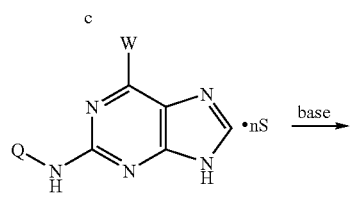

d e

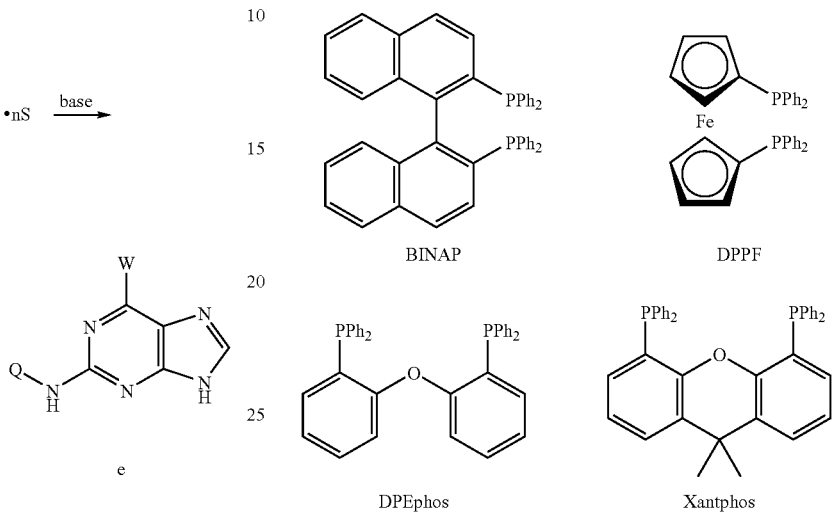

The preparation method includes the following steps:

1) firstly reacting the compound (a) with 2,3-dihydropyrane under catalysis of catalysts such as paratoluenesulfonic acid, pyridinium salt of paratoluenesulfonic acid or acidic resin or other catalyst to protect 9-nitrogen of purin; wherein the reacting molar ratio of compound (a) to 2,3-dihydropyrane is about 1:1~5; then in the presence of depickling solvent such as triethylamine, sodium carbonate, potassium carbonate or sodium bicarbonate, condensating with W to obtain compound (b); wherein the molar ratio of compound (a) to W is about 1:1~5, the reaction temperature of condensating with W is about 20~100° C., preferably is about 40~60° C.;

2) undergoing catalytic coupling reaction and deprotecting & salt-forming reaction of deprotecting group of compound (b) and Q-NH$_2$, to obtain compound (d); wherein the molar ratio of compound (b) to Q-NH$_2$ is about 1:0.5~2.

In the catalytic coupling reaction, the ligand includes tri-o-tolylphosphine, tri-tert-butylphosphine, 2,2'-diphenylphosphine-1,1'-binaphthalene, 1,1'-diphenylphosphine-ferrocene, bis(2-diphenylphosphinophenyl)ether, 9,9-dimethyl-4,5-diphenylphosphine xanthene, or the ligand is the compounds of formula 1, 2, 3, 4, 5, 6, 7, 8, 9, 10 or 11; the catalyst is a transition metal catalyst of palladium or nickel such as PdCl$_2$, Pd(OAc)$_2$, Pd$_2$(dba)$_3$, Ni(OAc)$_2$ or Ni/C; The base is sodium tert-butoxide, potassium tert-butoxide, potassium carbonate, cesium carbonate or tripotassium phosphate. The solvent is aprotic solvent such as tetrahydrofuran, isopropyl ether, ethylene glycol dimethyl ether, dioxane, pyridine, 1-methyl-2-pyrrolidone (NMP), 1,3-dimethyltrimethylene urea (DMPU), toluene or xylene or mixed solvents comprising one or more selected from the above-mentioned solvents.

In the catalytic coupling reaction, the reaction temperature is about 15~150° C., preferably is about 55~120° C., or the reaction is carried out by using microwave heating. The deprotecting & salt-forming reaction of step 2 could be carried out under the acidic condition such as hydrochloric acid, sulphuric acid, hydrobromic acid, methanesulfonic acid, benzene sulfonic acid, paratoluenesulfonic acid, maleic acid, fumaric acid, lactic acid or citric acid, and so on. Wherein, the molar ratio of compound c to hydrochloric acid, sulphuric acid, hydrobromic acid, methanesulfonic acid, benzene sulfonic acid, paratoluenesulfonic acid, maleic acid, fumaric acid, lactic acid, or citric acid may be respectively 1:1~10.

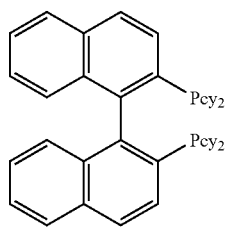

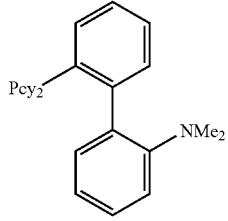

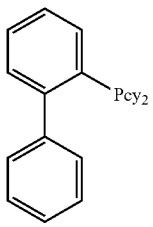

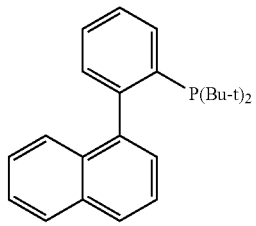

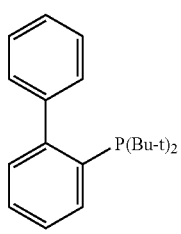

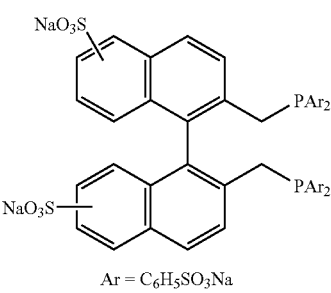

Ar = C₆H₅SO₃Na

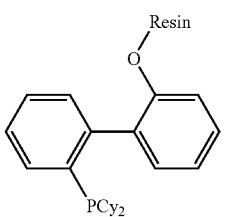

3) Neutralizing compound (d) with sodium carbonate, potassium carbonate, sodium hydroxide, or potassium hydroxide to obtain compound (e).

It is still another object of the present invention to provide a pharmaceutical composition, wherein the pharmaceutical composition is consisted of the compounds of formula (A) or salts or solvates thereof or the solvates of salts thereof and a pharmaceutical acceptable excipient. The salt is acidic addition salts produced by organic acid or inorganic acid, preferably the acid is hydrochloric acid, sulphuric acid, hydrobromic acid, methanesulfonic acid, benzene sulfonic acid, paratoluenesulfonic acid, maleic acid, fumaric acid, lactic acid, citric acid, or the salt is basic addition salts produced by organic base or inorganic base. The pharmaceutical composition is in the form of a tablet, a capsule, a pill, an oral liquid preparation, a granule, a powder, an injection, an implant or an external preparation.

The antitumor activity tests in vitro and in vivo show that the compounds A of the present invention has antitumor activity. The compounds have inhibitory effects on the growth of mouse Colon 26 and mouse S180 sarcoma. Compounds A or salts or solvates thereof or the solvates of salts thereof could be used to prepare a medicament for the treatment or prophylaxis of tumor diseases. The tumor diseases include lung cancer, liver cancer, leukemia, osteocarcinoma, pancreas cancer, skin cancer, melanoma, metrocarcinoma, oophoroma, rectal carcinoma, gastric carcinoma, colon cancer, breast carcinoma, salpingo carcinoma, endometrium carcinoma, cervix carcinoma, vagina carcinoma, carcinoma of vulva, esophagus carcinoma, small intestine carcinoma, endocrinium carcinoma, soft tissue sarcoma, urethra carcinoma, prostaticcancer, lymphocytoma, bladder cancer, kidney or ureter cancer, tumors of vertebral column, tumors in the neuroglia of the brain, and pituitary adenoma.

DETAILED DESCRIPTION AND PREFERRED EMBODIMENTS THEREO

Hereafter, the present invention will specifically be described with reference to examples. The examples are given only for illustration of the technical solution of the present invention and should not be construed to limit the present invention.

Examples 1~3

Preparation of Compounds of Formula I, II, III

Example 1

Preparation of Compound I

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min, and the above mixture is reacted at 50~60° C. for 3 h. The completion of reaction is checked with TCL analysis. Triethylamine (8 ml) is added to the bottle under refluxing allylamine (7 ml) is added thereto within 15 min, the above mixture is further reacted for 0.5 h. The completion of reaction is checked with TCL analysis, and then is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (12 g). The yield is about 77.3%.

2. In a 250 ml three-mouth flask, the solid purin (10.4 g) of the above step, 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and is reacted for about 2.5 h under refluxing. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain white conjugate (11.5 g). The yield is about 82.6% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). All the solid are completely dissolved to get a clear orange solution. Under refluxing the above mixture is further reacted for 1 h and is naturally cooled to room temperature after stopping stirring. After filtration, a filter cake is washed with acetone for 3 times and then dried in vacuum at 40° C. for 6 h to obtain (11.5 g) methanesulfonate.

$^1$H-NMR (DMSO-d$_6$+D$_2$O, ppm) δ: 4.29 (2H, s), 5.21 (1H, dd, J=2.0, 10.4 Hz), 5.32 (1H, dd, J=2.0, 17.2 Hz), 6.10 (1H, m), 7.98 (1H, dd, J=5.2, 8.4 Hz), 8.20 (1H, d, J=9.2 Hz), 8.34 (overlapped), 8.84 (2H, overlapped), 8.92 (1H, d, J=8.4 Hz), 9.08 (1H, dd, J=5.2, 1.2 Hz).

$^{13}$C-NMR (DMSO-d$_6$, ppm) δ: 43.0, 106.0, 113.2, 116.4, 121.6, 122.4, 128.7, 129.8, 134.2, 134.4, 138.9, 141.1, 142.5, 144.5, 149.3, 151.5, 155.4.

4. In a 100 ml flask, the methanesulfonate of the above step (10 g) and water (50 ml) are mixed and heated under stirring to dissolve them. 10% potassium carbonate solution is added thereto, and pH is adjusted to about 10, and then light yellow solid is separated out. The above mixture is cooled and filtered, a filter cake is washed with acetone and then dried in vacuum to obtain compound I (5.4 g).

(+)-ESI MS m/z: 318 [M+H]$^+$.

Example 2

Preparation of Compound II

Compound I (2.5 g) and bis(trimethylsilyl)acetamide (3.5 ml) are mixed in anhydrous acetonitrile (10 ml). The above mixture is stirred at room temperature for 1 h. A solution of tetraacetyl robofuranose (3.5 g) dissolved in acetonitrile (8 ml) and TMSTF (0.6 ml) are then added thereto and heated under refluxing for 5 h. BSA (0.7 ml) is added thereto and further stirred for 24 h. The completion of the reaction is checked with TLC analysis. The solvent is concentrated under reduced pressure and the residue is dissolved in methanol (15 ml). The above mixture is passed ammonia gas for 1.5 h. The solvent is removed under reduced pressure and the residue is purified by column chromatography on silica gel to obtain compound II (2.6 g).

(+)-ESI MS m/z: 450 [M+H]$^+$.

Example 3

Preparation of Compound III 1. 60% NaH (0.4 g) and anhydrous acetonitrile (50 ml) are mixed with compound I (2.5 g). The above mixture is stirred under protection of nitrogen for 30 min. 3,5-diparatoluenesulfonyl-2-deoxy-β-D-ribofuranose-1-chloride (3 g) is added in batches thereto within 10 min. After reacting at room temperature for 2 h and then filtration, a filtrate is concentrated to dry to obtain an oil substance. The oil substance is then purified by column chromatography to obtain solid substance (2.5 g).

2. The above solid substance, 50% sodium methoxide (0.6 g) and methanol (100 ml) are mixed and reacted under stirring at room temperature for 5 h. The pH of the above mixture is adjusted to neutral with acetic acid. The solvent is distilled off and the residue is purified by column chromatography to obtain compound III (1.3 g).

(+)-ESI MS m/z: 434 [M+H]$^+$.

Example 4~6

Preparation of Compounds of Formula IV, V, VI

Example 4

Preparation of Compound IV

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to at a temperature of 35° C., 2,3-dihydropyrane (12 ml) is added thereto within 5 min. And the above mixture is reacted at 50~60° C. for 3 h. The completion of reaction is checked with TCL analysis. Triethylamine (7.9 ml) is added to the bottle, and then pyrrolidine (7.8 ml) is added thereto within 15 min at the temperature, the above mixture is further reacted at the temperature for 0.5 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (12.3 g). The yield is about 75.6%.

2. In a 250 ml three-mouth flask, the purin of the above step (11.0 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (11.9 g). The yield is about 82.6% on the basis of aminoquinoline.

3. In a 250 ml one-mouth flask, the conjugate of the above step (10.0 g), acetone (60 ml) and water (60 ml) are mixed.

The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (12.0 g).

$^1$H-NMR (DMSO-d$_6$, ppm) δ: 2.06 (4H, s), 2.41 (6H, s), 3.93 (4H, brs), 7.95 (1H, dd, J=5.2 Hz, J=8.4 Hz), 8.17 (1H, d, J=9.2 Hz), 8.31 (1H, dd, J=2.4 Hz, J=9.4 Hz), 8.45 (1H, s), 8.85 (1H, d, J=2.0 Hz), 8.90 (1H, d, J=8.4 Hz), 9.04 (1H, d, J=4 Hz), 10.03 (exchange of 1H, s, D$_2$O disappeared).

4. In a 100 ml flask, the methanesulfonic salt of the above step (10 g) and water (60 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound IV (5.4 g).

Example 5

Preparation of Compound V

Compound IV (2.5 g) and bis(trimethylsilyl)acetamide (3.2 ml) are mixed in anhydrous acetonitrile (10 ml). The above mixture is stirred at room temperature for 1 h. A solution of tetraacetyl robofuranose (3.5 g) dissolved in acetonitrile (8 ml) and TMSTF (0.6 ml) are then added thereto and are heated under refluxing for 5 h. BSA (0.7 ml) is added thereto and further stirred for 24 h. The completion of the reaction is checked with TLC analysis. The solvent is concentrated under reduced pressure and the residue is dissolved in methanol (15 ml). The above mixture is passed ammonia gas for 1.5 h. The solvent is removed under reduced pressure and the residue is purified by column chromatography on silica gel to obtain compound V (2.3 g).

(+)-ESI MS m/z: 464 [M+H]$^+$.

Example 6

Preparation of Compound VI 1. 60% NaH (0.4 g) and anhydrous acetonitrile (50 ml) are mixed with compound IV (2.5 g). The above mixture is stirred under nitrogen protection for 30 min. 3, 5-diparatoluenesulfonyl-2-deoxy-β-D-ribofuranose-1-chloride (2.9 g) is added in batches thereto within 10 min. The above mixture is further reacted for 2 h. After filtration, a filtrate is concentrated to dry to obtain an oil substance. The oil substance is then purified by column chromatography to obtain solid substance (2.5 g).

2. The above solid substance, 50% sodium methoxide (0.7 g) and methanol (100 ml) are mixed and reacted under stirring at room temperature for 5 h. The pH of the above mixture is adjusted to neutral with acetic acid. The solvent is distilled off and the residue is purified by column chromatography to obtain compound VI (1.4 g).

(+)-ESI MS m/z: 448 [M+H]$^+$.

Example 7~9

Preparation of Compounds of Formula VII, VIII, IX

Example 7

Preparation of Compound VII

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The reaction mixture is reacted at 50~60° C. for 3 h. The completion of reaction is checked with TCL analysis. Methylamine hydrochloride (4.6 g) is added to the bottle, and then triethylamine (21 ml) is added thereto at the temperature within 30 min, and the above mixture is reacted at the temperature for 1 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amounts of solid is separated out. After filtration, a filter cake is washed with ethyl acetate for 3 times and then dried in vacuum at 50° C. for 5 h to obtain solid purin (11.0 g). The yield is about 77.7%.

2. In a 250 ml three-mouth flask, the purin of the above step (10.0 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain conjugate (10.7 g). The yield is about 82.2% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). The above mixture is further reacted for 1 h under refluxing and is naturally cooled to room temperature after stopping stirring. After filtration, a filter cake is washed with acetone for 3 times and then dried in vacuum at 40° C. for 6 h to obtain methanesulfonate (11.3 g).

$^1$H-NMR (DMSO-d$_6$, ppm) δ: 2.44 (6H, s), 3.15 (3H, s), 7.95 (1H, dd, J=5.2 Hz, J=8.0 Hz), 8.18 (1H, d, J=8.8 Hz), 8.33 (1H, dd, J=2.4 Hz, J=9.4 Hz), 8.70 (1H, s), 8.86 (1H, d, J=2.0 Hz), 8.91 (1H, d, J=8.4 Hz), 9.05 (1H, dd, J=1.2 Hz, J=5.2 Hz), 10.14 (exchange of 1H, s, D$_2$O disappeared).

4. In a 100 ml flask, the methanesulfonate of the above step (10 g) and water (50 ml) are mixed and heated under stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound VII (5.2 g).

Example 8

Preparation of Compound VIII

Free base of compound VII (2.5 g) and bis(trimethylsilyl) acetamide (3.7 ml) are mixed in anhydrous acetonitrile (10 ml). The above mixture is stirred at room temperature for 1 h. A solution of tetraacetyl robofuranose (3.5 g) dissolved in acetonitrile (8 ml) and TMSTF (0.6 ml) are then added thereto and are headed under refluxing for 5 h. BSA (0.7 ml) is added thereto under stirring for 24 h. The completion of the reaction is checked with TLC analysis. The solvent is concentrated under reduced pressure and the residue is dissolved in methanol (15 ml). The above mixture is passed ammonia gas for 1.5 h. The solvent is removed under reduced pressure and the residue is purified by column chromatography on silica gel to obtain compound VIII (2.7 g).

(+)-ESI MS m/z: 424 [M+H]$^+$.

Example 9

Preparation of Compound IX 1. 60% NaH (0.42 g) and anhydrous acetonitrile (50 ml) are mixed with compound VII (2.5 g). The above mixture is stirred under nitrogen protection for 30 min. 3,5-diparatoluenesulfonyl-2-deoxy-β-D-ribofuranose-1-chloride (3.5 g) is added in batches thereto within 10 min. Tthe above mixture is reacted for 2 h. After filtration, a filtrate is concentrated to dry to obtain an oil substance. The oil substance is then purified by column chromatography to obtain a solid substance (2.3 g).

2. The above solid substance, 50% sodium methoxide (0.75 g) and methanol (100 ml) are mixed and reacted under stirring at room temperature for 5 h. The pH of the above mixture is adjusted to neutral with acetic acid. The solvent is distilled off and the residue is purified by column chromatography to obtain compound IX (1.2 g).

(+)-ESI MS m/z: 408 [M+H]$^+$.

Example 10

Preparation of Compound X

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (7.9 ml) is added to the bottle, and DL-aminopropanol (7.0 ml) is added thereto under the temperature. The above mixture is reacted under the temperature for 1 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amounts of solid is separated out. After filtration, a filter cake is washed with ethyl acetate for 3 times and then dried in vacuum at 50° C. for 5 h to obtain solid purin (11.6 g). The yield is about 70.4%.

2. In a 250 ml three-mouth flask, the purin of the above step (11.6 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction is cooled to room temperature. After filtration, a filter cake is completely washed with ethylene glycol dimethyl ether for 2 times, and a filtrate is concentrated to dry and the residue is purified by column chromatography on silica gel to obtain conjugate (11.5 g). The yield is about 79.0% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). All the solid substances are dissolved to get a clear solution. The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (12.3 g).

$^1$H-NMR (DMSO-d$_6$, ppm) δ: 1.32 (3H, d, J=6.4 Hz), 2.44 (6H, s), 3.63 (2H, m), 4.43 (1H, brs), 7.96 (1H, dd, J=5.2 Hz, J=8.4 Hz), 8.00 (1H, brs), 8.19 (1H, d, J=9.2 Hz), 8.29 (1H, dd, J=2.4 Hz, J=9.4 Hz), 8.82 (1H, s), 8.85 (1H, d, J=2.0 Hz), 8.90 (1H, d, J=8.4 Hz), 9.05 (1H, dd, J=1.2 Hz, J=5.2 Hz), 10.18 (1H, s).

4. In a 100 ml flask, the methanesulfonate of the above step (12 g) and water (60 ml) are mixed and heated under stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound X (6.5 g).

(+)-ESI MS m/z: 335 [M+H]$^+$.

Example 11

Preparation of Compound XI

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (7.9 ml) is added to the bottle, and L-aminopropanol (7.0 ml) is added thereto. The above mixture is reacted at the temperature for 1 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (12.2 g). The yield is about 74.0%.

2. In a 250 ml three-mouth flask, the purin of the above step (11.6 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (12.1 g). The yield is about 83.2% on the basis of aminoquinoline.

3. In a 250 ml one-mouth flask, the compound (10.0 g) of the above step, acetone (60 ml) and water (60 ml) are mixed. The above mixture is stirred and heated followed by the addition of methanesulfonic acid (5 ml). The above mixture is further reacted under refluxing for 1 h and then is naturally cooled to room temperature after stopping stirring. After filtration, a filter cake is washed with acetone for 3 times and then dried in vacuum at 40° C. for 6 h to obtain methanesulfonate (11.9 g).

$^1$H-NMR (DMSO-d$_6$, ppm) δ: 1.32 (3H, d, J=6.8 Hz), 2.44 (6H, s), 3.63 (2H, m), 4.43 (1H, brs), 7.96 (1H, dd, J=5.2 Hz, J=8.4 Hz), 8.01 (1H, brs), 8.19 (1H, d, J=9.2 Hz), 8.29 (1H, dd, J=2.4 Hz, J=9.4 Hz), 8.82 (1H, s), 8.85 (1H, d, J=2.4 Hz), 8.90 (1H, d, J=8.8 Hz), 9.05 (1H, dd, J=1.2 Hz, J=5.2 Hz), 10.19 (1H, s).

4. In a 100 ml flask, the methanesulfonate (11 g) of the above step and water (50 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XI (5.8 g).

Example 12

Preparation of Compound XII

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Methylpiperazine (9.0 g) and triethylamine (8 ml) are added to the bottle. The above mixture is reacted at the temperature for 1 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum for 5 h at to obtain solid purin (12.0 g). The yield is about 67.4%.

2. In a 250 ml three-mouth flask, the purin of the above step (11.8 g), 6-aminoquinoline (5.0 g), catalyst $Pd(OAc)_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (12.0 g). The yield is about 77.8% on the basis of aminoquinoline.

3. In a 250 ml one-mouth flask, the compound of the above step (10.0 g), acetone (60 ml) and water (60 ml) are mixed. The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (11.5 g).

4. In a 100 ml flask, the methanesulfonate of the above step (11 g) and water (60 ml) are mixed and heated under stirring to dissolve them. 10% potassium carbonate solution is added thereto, and the pH is adjusted to about 10, then light yellow solid is separated out. The above mixture is cooled and filtered, a filter cake is washed with acetone and then dried in vacuum to obtain compound XII (5.9 g).

(+)-ESI MS m/z: 361 [M+H]$^+$.

Example 13

Preparation of Compound XIII

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (8 ml) is added to the bottle, and diallylamine (11.4 ml) is added thereto at the temperature within 20 min, the above mixture is reacted at the temperature for 0.5 h. The completion of reaction is checked with TCL analysis. The above mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (12.9 g). The yield is about 73.1%.

2. In a 250 ml three-mouth flask, the purin of the above step (12.0 g), 6-aminoquinoline (5.0 g), catalyst $Pd(OAc)_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain white conjugate (12.2 g). The yield is about 79.7% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). All the solid substances are dissolved to get a clear solution. The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (10.8 g).

$^1$H-NMR (DMSO-d6, ppm) δ: 2.44 (6H, s), 4.61 (4H, s), 5.19-5.27 (4H, m), 6.01 (2H, m), 7.98 (1H, dd, J=5.6 Hz, J=8.6 Hz), 8.14-8.18 (2H, m), 8.32 (1H, dd, J=2.4 Hz, J=9.2 Hz), 8.82 (1H, d, J=2.0 Hz), 8.86 (1H, d, J=8.8 Hz), 9.04 (1H, dd, J=1.6 Hz, J=5.4 Hz), 9.91 (exchange of 1H, s, $D_2O$ disappeared).

4. In a 100 ml flask, the methanesulfonate of the above step (10 g) and water (50 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XIII (5.6 g).

Example 14

Preparation of Compound XIV

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (8 ml) is added to the bottle, and piperidine (9.2 ml) is added thereto at the temperature within 20 min. The above mixture is reacted at the temperature for 0.5 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (12.8 g). The yield is about 75.2%.

2. In a 250 ml three-mouth flask, the purin of the above step (11.5 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (11.3 g). The yield is about 75.9% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (11.7 g).

$^1$H-NMR (DMSO-d6, ppm) δ: 1.70 (6H, m), 2.44 (6H, s), 4.19 (4H, s), 7.99 (1H, dd, J=5.2 Hz, J=8.2 Hz), 8.19 (2H, m), 8.32 (1H, dd, J=2.0 Hz, J=9.4 Hz), 8.79 (1H, d, J=2.0 Hz), 8.91 (1H, d, J=8.0 Hz), 9.05 (1H, dd, J=1.2 Hz, J=5.2 Hz), 9.95 (exchange of 1H, s, D$_2$O disappeared).

4. In a 100 ml flask, the methanesulfonate of the above step (11 g) and water (60 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XIV (6.0 g).

Example 15

Preparation of Compound XV

1. In a 100 ml three-mouth bottle 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (8 ml) is added to the bottle, and N-ethylpiperazine (10.3 g) is added thereto at the temperature within 20 min. The above mixture is reacted at the temperature for 0.5 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then is dried in vacuum at 50 for 5 h to obtain solid purin (13.0 g). The yield is about 70.0%.

2. In a 250 ml three-mouth flask, the purin of the above step (12.2 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (13.2 g). The yield is about 83.0% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (10.9 g).

$^1$H-NMR (DMSO-d6, ppm) δ: 1.30 (3H, d, J=7.4 Hz), 2.43 (6H, s), 3.21 (4H, m), 3.59 (2H, m), 3.70 (2H, m), 5.45 (2H, m), 7.99 (1H, dd, J=5.2 Hz, J=8.4 Hz), 8.08 (1H, brs), 8.20 (1H, d, J=9.2 Hz), 8.34 (1H, dd, J=2.0 Hz, J=9.4 Hz), 8.82 (1H, d, J=2.4 Hz), 8.98 (1H, d, J=8.4 Hz), 9.05 (1H, dd, J=1.2 Hz, J=5.6 Hz), 9.77 (1H, brs), 9.93 (1H, s).

4. In a 100 ml flask, the methanesulfonate of the above step (10 g) and water (50 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XV (5.8 g).

Example 16

Preparation of Compound XVI

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (7.9 ml) is added to the bottle, and morpholine (7.9 ml) is added thereto at the temperature. The above mixture is reacted at the temperature for 1 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (11.2 g). The yield is about 65.4%.

2. In a 250 ml three-mouth flask, the purin of the above step (11.6 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (11.5 g). The yield is about 76.8% on the basis of aminoquinoline.

3. In a 250 ml one-mouth flask, the compound of the above step (10.0 g), acetone (60 ml) and water (60 ml) are mixed. The above mixture is stirred and heated followed by the addition of methanesulfonic acid (5 ml). All the solid substances are dissolved to get a clear solution. The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (11.7 g).

$^1$H-NMR (DMSO-d6, ppm) δ: 2.42 (6H, s), 3.78 (4H, m), 4.22 (4H, s), 7.98 (1H, dd, J=5.2 Hz, J=8.4 Hz), 8.10 (1H, s), 8.17 (1H, d, J=9.2 Hz), 8.32 (1H, dd, J=2.0 Hz, J=9.4 Hz), 8.80 (1H, d, J=1.6 Hz), 8.94 (1H, d, J=8.8 Hz), 9.04 (1H, d, J=5.2 Hz), 9.89 (1H, s).

4. In a 100 ml flask, the methanesulfonate of the above step (10 g) and water (50 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XVI (5.4 g).

Example 17

Preparation of Compound XVII

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (8 ml) is added to the bottle, and isopropylamine (7.7 ml) is added thereto under refluxing within 15 min. The above mixture is further reacted at the temperature for 0.5 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (10.8 g). The yield is about 70.0%.

2. In a 250 ml three-mouth flask, the purin of the above step (11.0 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain white conjugate (11.7 g). The yield is about 83.6% on the basis of aminoquinoline.

3. In a 250 ml one-mouth flask, the compound of the above step (10.0 g), acetone (60 ml) and water (60 ml) are mixed. The above mixture is stirred and heated followed by the addition of methanesulfonic acid (5 ml). All the solid substances are dissolved to get a clear solution. The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (9.7 g).

$^1$H-NMR (DMSO-d6, ppm) δ: 1.35 (6H, d, J=6.4 Hz), 2.47 (6H, s), 4.35 (1H, brs), 7.97 (1H, dd, J=5.2 Hz, J=8.6 Hz), 8.09 (1H, brs), 8.20 (1H, d, J=9.2 Hz), 8.31 (1H, dd, J=2.0 Hz, J=9.4 Hz), 8.83 (2H, overlapped), 8.89 (1H, d, J=8.4 Hz), 9.06 (1H, dd, J=1.2 Hz, J=5.2 Hz), 10.20 (1H, s).

(+)-ESI MS m/z: 320 [M+H]$^+$.

4. In a 100 ml flask, the methanesulfonate of the above step (9 g) and water (50 ml) are mixed and heated with stirring to dissolve them. 10% potassium carbonate solution is added thereto, and the pH is adjusted to about 10, and then light yellow solid is separated out. The above mixture is cooled and filtered, a filter cake is washed with acetone and then dried in vacuum to obtain compound XVII (4.8 g).

Example 18

Preparation of Compound XVIII

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (8 ml) is added to the bottle, and diethylamine (9.6 ml) is added thereto at the temperature within 20 min, the above mixture is reacted at the temperature for 0.5 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50 for 5 h to obtain solid purin (12.3 g). The yield is about 75.1%.

2. In a 250 ml three-mouth flask, the purin of the above step (11.0 g), 6-aminoquinoline (5.0 g), catalyst Pd(OAc)$_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (11.9 g). The yield is about 82.2% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (11.3 g).

$^1$H-NMR (DMSO-d6, ppm) δ: 1.30 (6H, t, J=7.0 Hz), 2.44 (6H, s), 3.97 (4H, brs), 8.02 (1H, dd, J=5.6 Hz, J=8.4 Hz), 8.21 (1H, d, J=9.2 Hz), 8.31-8.35 (2H, m), 8.85 (1H, d, J=2.0 Hz), 8.94 (1H, d, J=8.4 Hz), 9.09 (1H, d, J=5.2 Hz).

4. In a 100 ml flask, the methanesulfonate of the above step (10 g) and water (50 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XVIII (5.5 g).

(+)-ESI MS m/z: 334 [M+H]$^+$.

Example 19

Preparation of Compound XIX

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (8 ml) is added to the bottle, and methylethylamine (7.7 ml) is added thereto under refluxing within 20 min, the above mixture is reacted at the temperature for 0.5 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid (10.3 g). The yield is about 65.9%.

2. In a 250 ml three-mouth flask, 6-aminoquinoline (5.0 g), 2-chloro-N-methyl-N-ethyl-9-(tetrahydro-2H-pyran-2-yl)-9H-purine-6-amine (10.3 g), catalyst $Pd(OAc)_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (10.5 g). The yield is about 75.0% on the basis of aminoquinoline.

3. In a 250 ml one-mouth flask, the compound of the above step (10.0 g), acetone (60 ml) and water (60 ml) are mixed. The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (11.2 g).

4. In a 100 ml flask, the methanesulfonate of the above step (10 g) and water (50 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XIX (5.4 g).

Compound XIX: (+)-ESI MS m/z: 320 $[M+H]^+$.

Example 20

Preparation of Compound XX

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Dimethylamine hydrochloride (7.3 g) is added to the bottle, and triethylamine (22 ml) is added thereto at the temperature within 30 min, the above mixture is further reacted at the temperature for 0.5 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (8.9 g). The yield is about 59.8%.

2. In a 250 ml three-mouth flask, the purin of the above step (8.9 g), 6-aminoquinoline (4.5 g), catalyst $Pd(OAc)_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for about 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (10.5 g). The yield is about 86.4% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). All the solid substances are dissolved to get a clear solution. The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (9.8 g).

4. In a 100 ml flask, the methanesulfonate of the above step (9 g) and water (50 ml) are mixed and heated under stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound XX (4.9 g).

(+)-ESI MS m/z: 306 $[M+H]^+$.

Example 21

Preparation of Compound XXI

1. In a 100 ml three-mouth bottle, 2,6-dichloropurine (10 g), ethyl acetate (50 ml), pyridinium salt of paratoluenesulfonic acid (0.2 g) are mixed. The above mixture is stirred and heated to a temperature of 35° C., 2,3-dihydropyrane (12 ml) is added thereto within 5 min. The above mixture is reacted at 50~60° C. for 3 h. The completion of reaction is checked with TCL analysis. Triethylamine (8 ml) and piperazine (7.3 ml) are added to the bottle within 20 min, the above mixture is reacted at the temperature for 1 h. The completion of reaction is checked with TCL analysis. The reaction mixture is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid purin (12.4 g). The yield is about 72.7%.

2. In a 250 ml three-mouth flask, the purin of the above step (12.0 g), 6-aminoquinoline (5.0 g), catalyst $Pd(OAc)_2$ (0.3 g), ligand 7 (0.3 g), sodium tert-butoxide (5.4 g) and ethylene glycol dimethyl ether (100 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (12.7 g). The yield is about 85.0% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). All the solid substances are dissolved to get a clear solution. The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (12.1 g).

$^1$H-NMR (DMSO-d6, ppm) δ: 2.43 (9H, s), 3.22 (2H, m), 3.54-3.66 (4H, m), 5.41 (2H, m), 8.01 (1H, dd, J=5.2 Hz, J=8.6 Hz), 8.12 (1H, s), 8.21 (1H, d, J=9.6 Hz), 8.34 (1H, dd, J=2.0 Hz, J=9.0 Hz), 8.83 (1H, d, J=2.0 Hz), 8.99 (1H, d, J=8.8 Hz), 9.06 (1H, d, J=4.2 Hz), 9.98 (exchange of 2H, brs, D$_2$O disappeared).

4. In a 100 ml flask, the methanesulfonate of the above step (11 g) and water (60 ml) are mixed. 10% potassium carbonate solution is then added thereto, and the pH is adjusted to about 10, then solid is separated out. The above mixture is cooled and filtered, a filter cake is washed with acetone and then dried in vacuum to obtain compound XXI (5.3 g).

Example 22

Preparation of Compound XXII

1. In a 3000 ml three-mouth bottle, 2,6-dichloropurine (300 g), ethyl acetate (1500 ml), pyridinium salt of paratoluenesulfonic acid (3 g) are mixed. The above mixture is stirred and heated to a temperature of 35° C., 2,3-dihydropyrane (360 ml) is added thereto within 30 min. The above mixture is reacted at 50~60° C. for 5 h. The completion of reaction is checked with TCL analysis. Triethylamine (240 ml) is added to the bottle, and cyclopropylamine (204 ml) is added thereto under refluxing within 30 min. The above mixture is reacted at the temperature for 0.5 h. The completion of reaction is checked with TCL analysis. The reaction is cooled to room temperature. After filtration, a filter cake is completely washed with ethyl acetate, and a filtrate is washed with water for 3 times and delaminated. Organic layer is concentrated till large amount of solid is separated out. After filtration, a filter cake is washed with ethyl acetate for 3 times and then dried in vacuum at 50° C. for 5 h to obtain solid compound 2-choro-N-cyclopropyl-9-(tetrahydro-2H-pyran-2-yl)-9H-purine-6-amine (364 g).

2. In a 250 ml three-mouth flask, 6-amino-8-methylquinoline (5.0 g), 2-choro-N-cyclopropyl-9-(tetrahydro-2H-pyran-2-yl)-9H-purine-6-amine (10.2 g), catalyst Pd(OAc)$_2$ (0.3 g), ligand 7 (0.3 g), sodium tert-butoxide (5 g) and ethylene glycol dimethyl ether (100 ml) are added in turn. The above mixture is stirred and heated to reflux, and the above mixture is reacted under refluxing for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (11.2 g). The yield is about 85.3% on the basis of aminoquinoline.

3. In a 250 ml one-mouth flask, the conjugate of the above step (10.0 g), acetone (60 ml) and water (60 ml) are mixed. The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (11.3 g).

$^1$H-NMR (DMSO-d6, ppm) δ: 0.75 (2H, s), 0.95 (2H, m), 2.41 (6H, s), 2.76 (3H, s), 3.12 (1H, brs), 7.84 (1H, dd, J=4.8 Hz, J=8.2 Hz), 8.12 (1H, s), 8.50 (exchange of 1H, brs, D$_2$O disappeared), 8.71 (3H, m), 8.93 (1H, d, J=4.0 Hz), 10.05 (exchange of 1H, s, D$_2$O disappeared).

4. In a 100 ml flask, the methanesulfonate of the above step (10 g) and water (50 ml) are mixed and heated under stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound XXII (5.3 g).

Example 23

Preparation of Compound XXIII

1. In a 250 ml three-mouth flask, 6-amino-8-methoxylquinoline (5.0 g), 2-choro-N-cyclopropyl-9-(tetrahydro-2H-pyran-2-yl)-9H-purine-6-amine (9.3 g), catalyst Pd(OAc)$_2$ (0.25 g), ligand 7 (0.25 g), sodium tert-butoxide (4.5 g) and ethylene glycol dimethyl ether (100 ml) are added in turn. The above mixture is stirred and heated to reflux, and the above mixture is reacted under refluxing for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (11.0 g). The yield is about 88.8% on the basis of aminoquinoline.

2. In a 250 ml one-mouth flask, the compound of the above step (10.0 g), acetone (60 ml) and water (60 ml) are mixed. The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (11.8 g).

$^1$H-NMR (DMSO-d$_6$, ppm) δ: 0.73 (2H, s), 0.93 (2H, m), 2.37 (6H, s), 3.14 (1H, brs), 4.13 (3H, s), 7.96 (2H, m), 8.30 (exchange of 1H, s, D$_2$O disappeared), 8.64 (2H, brs), 8.86 (2H, m), 10.01 (exchange of 1H, s, D$_2$O disappeared).

3. In a 100 ml flask, the methanesulfonate of the above step (11 g) and water (60 ml) are added and heated under stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound XXIII (6.1 g).

Example 24

Preparation of Compound XXIV

1. In a 250 ml three-mouth flask, 6-amino-8-trifluoromethylquinoline (5.0 g), 2-choro-N-cyclopropyl-9-(tetrahydro-2H-pyran-2-yl)-9H-purine-6-amine (7.6 g), catalyst Pd(OAc)$_2$ (0.3 g), ligand 7 (0.3 g), sodium tert-butoxide (4.0 g) and ethylene glycol dimethyl ether (100 ml) are added in turn. The above mixture is stirred and heated to reflux, and the above mixture is reacted under refluxing for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (8.5 g). The yield is about 76.8% on the basis of aminoquinoline.

2. In a 250 ml one-mouth flask, the conjugate of the above step (8 g), acetone (50 ml) and water (40 ml) are mixed. The above mixture is stirred and heated followed by the addition of methanesulfonic acid (3.8 ml). All the solid substances are dissolved to get a clear solution. The above mixture is further reacted under refluxing for 1 h and is naturally cooled to room temperature after stopping stirring. After filtration, a filter cake is washed with acetone for 3 times and then dried in vacuum at 40° C. for 6 h to obtain a solid methanesulfonate (8.7 g).

$^1$H-NMR (DMSO-d6, ppm) δ: 0.69 (2H, s), 0.76 (2H, brs), 2.40 (6H, s), 2.97 (1H, brs), 7.77 (1H, dd, J=4.0 Hz, J=8.2 Hz), 8.46 (3H, m), 8.53 (1H, d, J=8.4 Hz), 8.86 (exchange of 1H, brs, D$_2$O disappeared), 9.10 (1H, d, J=4.0 Hz), 9.46 (exchange of 1H, brs, D$_2$O disappeared).

3. In a 100 ml flask, the methanesulfonate of the above step (8 g) and water (40 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XXIV (4.5 g).

Example 25

Preparation of Compound XXV

1. In a 250 ml three-mouth flask, 2-methyl-4-aminoquinoline (5.0 g), 2-choro-N-cyclopropyl-9-(tetrahydro-2H-pyran-2-yl)-9H-purine-6-amine (10.2 g), catalyst Pd(OAc)$_2$ (0.3 g), ligand 7 (0.3 g), sodium tert-butoxide (5.0 g) and ethylene glycol dimethyl ether (100 ml) are added in turn. The above mixture is stirred and heated to reflux, and the above mixture is reacted under refluxing for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (11.8 g). The yield is about 89.9% on the basis of aminoquinoline.

2. In a 250 ml one-mouth flask, the conjugate of the above step (10 g), acetone (60 ml) and water (60 ml) are mixed. The above mixture is stirred and heated followed by the addition of methanesulfonic acid (5 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain solid methanesulfonate (10.9 g).

$^1$H-NMR (DMSO-d6, ppm) δ: 0.75 (2H, m), 0.87 (2H, m), 2.37 (6H, s), 2.79 (3H, s), 3.10 (1H, brs), 7.78 (1H, m), 8.02 (2H, m), 8.35 (exchange of 1H, brs, D$_2$O disappeared), 8.60 (1H, m), 8.91 (2H, m), 10.68 (exchange of 1H, s, D$_2$O disappeared).

3. In a 100 ml flask, the methanesulfonate of the above step (10 g) and water (50 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XXV (5.2 g).

Example 26

Preparation of Compound XXVI

1. In a 250 ml three-mouth flask, 8-choro-6-aminoquinoline (5.0 g), 2-choro-N-cyclopropyl-9-(tetrahydro-2H-pyran-2-yl)-9H-purine-6-amine (9.0 g), catalyst Pd(OAc)$_2$ (0.25 g), ligand 7 (0.25 g), sodium tert-butoxide (4.5 g) and ethylene glycol dimethyl ether (100 ml) are added in turn. The above mixture is stirred and heated to reflux, and the above mixture is reacted under refluxing for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (4.6 g). The yield is about 37.7% on the basis of aminoquinoline.

2. In a 250 ml one-mouth flask, the conjugate of the above step (4.5 g), acetone (30 ml) and water (30 ml) are mixed. The above mixture is stirred and heated followed by the addition of methanesulfonic acid (2 ml). All the solid substances are dissolved to get a clear solution. The above mixture is further reacted under refluxing for 1 h and is naturally cooled to room temperature after stopping stirring. After filtration, a filter cake is washed with acetone for 3 times and then dried in vacuum at 40° C. for 6 h to obtain solid methanesulfonate (4.5 g).

$^1$H-NMR (DMSO-d6, ppm) δ: 0.74 (2H, m), 0.98 (2H, m), 2.42 (6H, s), 3.07 (1H, s), 7.63 (1H, m), 8.32 (1H, d, J=8.4 Hz), 8.47-8.54 (2H, m), 8.74-8.87 (2H, m), 10.04 (exchange of 1H, brs, D$_2$O disappeared).

3. In a 100 ml flask, the methanesulfonate of the above step (4 g) and water (25 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XXVI (2.3 g).

Example 27

Preparation of Compound XXVII

1. In a 250 ml three-mouth flask, 3-aminopyridine (5.0 g), 2-choro-N-cyclopropyl-9-(tetrahydro-2H-pyran-2-yl)-9H-purine-6-amine (16.0 g), catalyst Pd(OAc)$_2$ (0.4 g), ligand 7 (0.4 g), sodium tert-butoxide (7.5 g) and ethylene glycol dimethyl ether (130 ml) are added in turn. The above mixture is stirred and heated to reflux, and the above mixture is reacted under refluxing for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (12.9 g). The yield is about 69.1% on the basis of aminopyridine.

2. In a 250 ml one-mouth flask, the compound of the above step (10 g), acetone (60 ml) and water (60 ml) are mixed. The above mixture is stirred and heated followed by the addition of methanesulfonic acid (6 ml). The above mixture is further reacted under refluxing for 1 h and is naturally cooled to room temperature after stopping stirring. After filtration, a filter cake is washed with acetone for 3 times and then dried in vacuum at 40° C. for 6 h to obtain methanesulfonate (12 g).

$^1$H-NMR (DMSO-d6, ppm) δ: 0.68 (2H, m), 0.93 (2H, m), 2.38 (6H, s), 3.01 (1H, brs), 7.97 (1H, dd, J=5.6 Hz, J=8.8 Hz), 8.24 (exchange of 1H, brs, $D_2O$ disappeared), 8.46 (1H, d, J=5.2 Hz), 8.54 (1H, brs), 8.69 (1H, d, J=8.4 Hz), 9.66 (1H, s), 10.25 (exchange of 1H, brs, $D_2O$ disappeared).

3. In a 100 ml flask, the methanesulfonate of the above step (11 g) and water (60 ml) are mixed and heated with stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound XXVII (5.3 g).

Example 28

Preparation of Compound XXVIII

1. In a 250 ml three-mouth flask, 2-aminopyridine (5.0 g), 2-choro-N-cyclopropyl-9-(tetrahydro-2H-pyran-2-yl)-9H-purine-6-amine (16.0 g), catalyst Pd(OAc)$_2$ (0.4 g), ligand 7 (0.4 g), sodium tert-butoxide (7.5 g) and ethylene glycol dimethyl ether (130 ml) are added in turn. The above mixture is stirred and heated to reflux, and under refluxing the above mixture is reacted for about 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (10.5 g). The yield is about 56.0% on the basis of aminopyridine.

2. In a 250 ml one-mouth flask, the conjugate of the above step (10 g), acetone (60 ml) and water (60 ml) are mixed. The above mixture is stirred and heated followed by the addition of methanesulfonic acid (6 ml). Under refluxing the above mixture is further reacted for 1 h and is naturally cooled to room temperature after stopping stirring. After filtration, a filter cake is washed with acetone for 3 times and then dried in vacuum at 40° C. for 6 h to obtain methanesulfonate (11.7 g).

$^1$H-NMR (DMSO-d6, ppm) δ: 0.78 (2H, m), 0.98 (2H, m), 2.39 (6H, s), 3.06 (1H, brs), 7.30 (1H, m), 7.47 (1H, d, J=8.8 Hz), 8.14 (1H, m), 8.30 (1H, s), 8.47 (1H, s), 9.17 (exchange of 1H, brs, $D_2O$ disappeared), 11.71 (exchange of 1H, brs, $D_2O$ disappeared).

3. In a 100 ml flask, the methanesulfonate of the above step (11 g) and water (60 ml) are mixed and heated under stirring to dissolve them. 10% potassium carbonate solution is added thereto, and the pH is adjusted to about 10, then solid is separated out. The above mixture is cooled and filtered, a filter cake is washed with acetone and then dried in vacuum to obtain compound XXVIII (5.0 g).

Example 29

Preparation of Compound XXIX

1. In a 250 ml three-mouth flask, 4-aminopyridine (5.0 g), 2-choro-N-cyclopropyl-9-(tetrahydro-2H-pyran-2-yl)-9H-purine-6-amine (16.0 g), catalyst Pd(OAc)$_2$ (0.4 g), ligand 7 (0.4 g), sodium tert-butoxide (7.5 g) and ethylene glycol dimethyl ether (130 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (13.7) g. The yield is about 73.4% on the basis of aminopyridine.

2. In a 250 ml one-mouth flask, the conjugate of the above step (10 g), acetone (60 ml) and water (60 ml) are mixed. The above mixture is stirred and heated followed by the addition of methanesulfonic acid (6 ml). All the solid substances are dissolved to get a clear solution. Under refluxing the above mixture is further reacted for 1 h and is naturally cooled to room temperature after stopping stirring. After filtration, a filter cake is washed with acetone for 3 times and then dried in vacuum at 40° C. for 6 h to obtain methanesulfonate (10.9 g).

$^1$H-NMR (DMSO-d6, ppm) δ: 0.71 (2H, m), 0.92 (2H, m), 2.42 (6H, s), 3.05 (1H, brs), 8.38 (2H, brs), 8.54 (2H, m), 8.75 (1H, s), 11.03 (exchange of 1H, brs, $D_2O$ disappeared).

3. In a 100 ml flask, the methanesulfonate of the above step (10 g) and water (50 ml) are mixed and heated with stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound XXIX (5.0 g).

Example 30

Preparation of Compound XXX

1. In a 250 ml three-mouth flask, paranitroaniline (5.0 g), 2-choro-N-cyclopropyl-9-(tetrahydro-2H-pyran-2-yl)-9H-purine-6-amine (10.9 g), catalyst Pd(OAc)$_2$ (0.3 g), ligand 7 (0.3 g), sodium tert-butoxide (5.8 g) and ethylene glycol dimethyl ether (130 ml) are added in turn. The above mixture is stirred and heated to reflux, and under refluxing the above mixture is reacted for about 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (12.5 g). The yield is about 85.6% on the basis of aminopyridine.

2. In a 250 ml one-mouth flask, the conjugate of the above step (10 g), acetone (60 ml) and water (60 ml) are mixed. The above mixture is stirred and heated followed by the addition of methanesulfonic acid (5 ml). Under refluxing the above mixture is further reacted for 1 h and is naturally cooled to room temperature after stopping stirring. After filtration, a filter cake is washed with acetone for 3 times and then dried in vacuum at 40° C. for 6 h to obtain methanesulfonate (10.3 g).

$^1$H-NMR (DMSO-d6, ppm) δ: 0.70 (2H, m), 0.95 (2H, m), 2.48 (6H, s), 3.06 (1H, brs), 8.13 (2H, m), 8.19 (2H, m), 8.49 (1H, brs), 8.99 (1H, s), 10.26 (1H, s).

3. In a 100 ml flask, the methanesulfonate of the above step (10 g) and water (50 ml) are mixed and heated under stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound XXX (5.1 g).

Example 31

Preparation of Compound XXXI

1. In a 250 ml three-mouth flask, para-toluidine (5.0 g), 2-choro-N-cyclopropyl-9-(tetrahydro-2H-pyran-2-yl)-9H-purine-6-amine (13.7 g), catalyst Pd(OAc)$_2$ (0.4 g), ligand 7 (0.4 g), sodium tert-butoxide (7.5 g) and ethylene glycol dimethyl ether (130 ml) are added in turn. The above mixture is stirred and heated to reflux, and under refluxing the above mixture is reacted for 2.5 h. The completion of reaction is checked with TCL analysis. The reaction mixture is cooled to room temperature. After filtration, a filter cake is completely washed with ethylene glycol dimethyl ether for 2 times, and a filtrate is concentrated to dry and the residue is purified by column chromatography on silica gel to obtain a conjugate (12.3 g). The yield is about 72.3% on the basis of aminopyridine.

2. In a 250 ml one-mouth flask, the conjugate of the above step (10 g), acetone (60 ml) and water (60 ml) are mixed. The above mixture is stirred and heated followed by the addition of methanesulfonic acid (6 ml). Under refluxing the above mixture is further reacted for 1 h and then is naturally cooled to room temperature after stopping stirring. After filtration, a filter cake is washed with acetone for 3 times and then dried in vacuum at 40° C. for 6 h to obtain methanesulfonate (10.8 g).

$^1$H-NMR (DMSO-d6, ppm) δ: 0.79 (2H, m), 0.97 (2H, m), 2.34 (3H, s), 2.44 (6H, s), 7.21 (2H, d, J=8.4 Hz), 3.07 (1H, brs), 7.67 (2H, d, J=8.4 Hz), 8.49 (1H, s), 9.56 (1H, brs).

3. In a 100 ml flask, the methanesulfonate of the above step (10 g) and water (50 ml) are mixed and heated under stirring to dissolve them. 10% potassium carbonate solution is added thereto, and the pH is adjusted to about 10, and then solid is separated out. The above mixture is cooled and filtered, a filter cake is washed with acetone and then dried in vacuum to obtain compound XXXI (5.0 g).

Antitumor activity tests in vitro and in vivo are carried out to the parital compounds prepared from the above examples. Wherein the method of SRB, MTT is used in vitro, and the action time is about 72 h. Concrete datum of activity are shown in Table 1. Inhibitory effects of the compounds on the growth of mouse Conlon26 cancer are shown in Table 2, inhibitory effects of the compounds on the growth of mouse S180 sarcoma are shown in Table 3.

TABLE 1

Determination of anticancer activity of the compounds in vitro IC$_{50}$ (μM)

| serial number | compound | non-small cell lung cancer | colon cancer HT-29 | human liver cancer Bel-7402 | lymph cancer Ramos |
|---|---|---|---|---|---|
| 1 | ADR | 0.05 | 0.38 | 0.02 | 0.19 |
| 2 | I | 3.61 | 8.61 | 1.58 | 5.78 |
| 3 | IV | 2.28 | 0.38 | 0.67 | 0.67 |
| 4 | VII | 6.65 | 4.01 | 0.23 | 1.27 |
| 5 | X | 12.49 | 24.15 | 1.78 | 4.96 |
| 6 | XI | 17.23 | 18.29 | 4.58 | 5.95 |
| 7 | XIII | 1.71 | 1.94 | 3.46 | 3.01 |
| 8 | XIV | 1.33 | 2.22 | 4.62 | 2.93 |
| 9 | XV | 3.36 | 4.27 | 5.46 | 2.87 |
| 10 | XXI | 6.27 | 2.74 | 2.33 | 2.33 |
| 11 | XXIII | 13.18 | 5.72 | 5.91 | 2.63 |
| 12 | XXIV | 11.69 | >100 | >100 | >100 |
| 13 | XXV | 13.8 | 2.25 | 5.28 | 5.28 |
| 14 | XXVI | 3.11 | 3.13 | 1.29 | 1.29 |
| 15 | XXVIII | 61.41 | 81.41 | 80.19 | 51.91 |
| 16 | XXIX | 7.55 | 16.77 | 4.89 | 4.14 |
| 17 | XXX | 11.09 | >100 | >100 | >100 |

Note:
ADR is control drug, that is, adriamycin.

TABLE 2

Inhibitory effects of the compounds on the growth of mouse Conlon26 cancer

| Group | Compound | Dose (mg/kg) | Administration route | Iinitial body weight (g) | End body weight (g) | Tumor weight (g) | Tumor removed body weight (g) | Inhibition rate (%) |
|---|---|---|---|---|---|---|---|---|
| XC-4A | I | 150 | p.o. | 21.10 | 17.96 | 0.43 | 17.26 | 76.52 |
| XC-4A | I | 100 | p.o. | 19.47 | 18.15 | 0.69 | 17.46 | 62.25 |
| XC-4B | XX | 150 | p.o. | 19.90 | 18.68 | 0.38 | 18.31 | 79.47 |
| XC-4B | XX | 100 | p.o. | 19.64 | 18.74 | 0.51 | 18.23 | 72.31 |
| XC-4C | XII | 150 | p.o. | 19.16 | 18.28 | 0.91 | 17.36 | 50.16 |
| XC-4C | XII | 100 | p.o. | 19.06 | 19.16 | 1.19 | 17.98 | 35.18 |
| XC-4D | IV | 150 | p.o. | 20.10 | 18.41 | 0.83 | 17.57 | 54.45 |
| XC-4D | IV | 100 | p.o. | 20.09 | 19.32 | 1.22 | 18.10 | 33.31 |
|  | CTX | 30 | i.p. | 20.03 | 20.33 | 0.40 | 19.93 | 78.14 |
|  | Negative control |  |  | 19.78 | 20.44 | 1.83 | 18.61 |  |

Explanation:
p.o. means administration by oral gavage;
i.p. means administration by abdominal injection.
CTX means cyclophosphamide for injection.

TABLE 3

Inhibitory effects of the compounds on the growth of mouse S180 sarcoma

| Group | Compound | Dose (mg/kg) | Administration route | Initial body weight (g) | End body weight (g) | Tumor weight (g) | Tumor removed body weight (g) | Inhibition rate (%) |
|---|---|---|---|---|---|---|---|---|
| XC-4A | I | 200 | p.o. | 18.97 | 16.04 | 0.68 | 15.36 | 70.21 |
| XC-4A | I | 100 | p.o. | 19.74 | 18.32 | 0.71 | 17.61 | 68.93 |
| XC-4B | XX | 200 | p.o. | 19.58 | 16.80 | 0.61 | 16.20 | 73.38 |
| XC-4B | XX | 100 | p.o. | 19.96 | 16.53 | 0.63 | 15.90 | 72.19 |
| XC-4C | XII | 200 | p.o. | 19.46 | 21.35 | 1.21 | 20.14 | 46.96 |
| XC-4C | XII | 100 | p.o. | 19.22 | 22.58 | 1.63 | 20.94 | 28.19 |
| XC-4D | IV | 200 | p.o. | 19.49 | 19.12 | 1.02 | 18.10 | 55.37 |
| XC-4D | IV | 100 | p.o. | 18.99 | 20.77 | 1.55 | 19.22 | 31.95 |
|  | CTX | 30 | i.p. | 19.65 | 20.31 | 0.46 | 19.85 | 79.82 |
|  | Negative control |  |  | 18.77 | 23.04 | 2.28 | 20.77 |  |

Explanation:
p.o. means administration by oral gavage;
i.p. means administration by abdominal injection.
CTX means cyclophosphamide for injection.

Activity datum in vitro in Table 1 show that most of the compounds have certain antitumor activity, wherein compounds I, VII, XIII, XIV, XV, XXI, XXVI show higher antitumor activity to four different cancer cells, especially the activity of compound IV is the best. According to the determinated result of activity in vivo, while administration in 100 mg/kg dosage, compound I has better inhibitory effects on mouse Colon26 cancer and mouse S180 sarcoma. Compared with compound I, compound XX has better antitumor effects. While administration in 100 mg/kg dosage, inhibition rate of compound XX to mouse Colon26 cancer reaches 72.31%, and its inhibition rate to mouse S180 sarcoma reaches 72.19%.

We claim:

1. Compounds of formula (A) or salts or solvates thereof or the solvates of salts thereof:

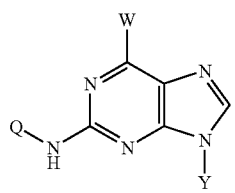

A wherein:
W represents an optionally monosubstituted $C_3$-$C_6$ straight or branched alkenyl or alkynyl amino, an optionally disubstituted $C_1$-$C_6$ straight or branched alkylamino, an optionally disubstituted $C_3$-$C_6$ straight or branched alkenyl or alkynyl amino;
W may also represent amino substituted by two different $C_1$-$C_6$ straight or branched alkane, or represent amino substituted by two different $C_3$-$C_6$ straight or branched olefin, or amino which one end is substituted by $C_1$-$C_6$ alkane and the other end is substituted by $C_3$-$C_6$ olefin, or an optionally substituted pyrrolidine, piperidine, morpholine or piperazidine;
the substituent represents $C_1$-$C_6$ straight or branched alkyl or halogen or hydroxyl;
Y represents H or a pharmaceutically acceptable saccharide, wherein the saccharide represents any one of the following formulas:

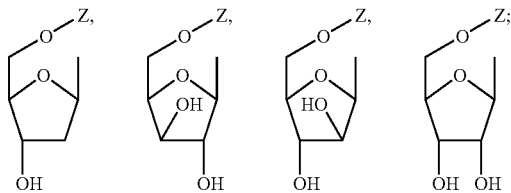

Z represents H or any one of the following formulas:

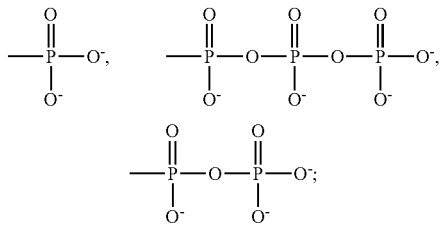

Q represents any one of the following formulas:

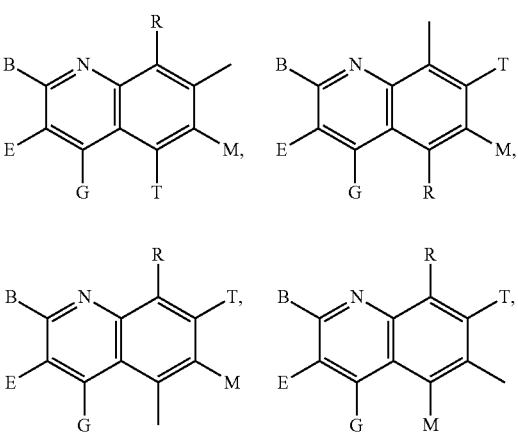

-continued

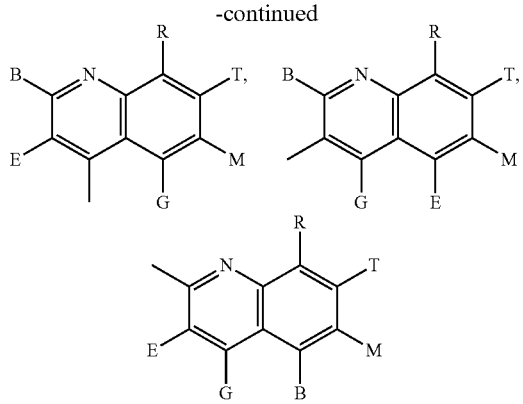

in the above formulas, B, E, G, R, T, M each independently represents a H or a $C_1$~$C_6$ straight or branched alkyl, or haloalkyl, a $C_3$~$C_6$ cycloalkyl, halogen, CN, $NH_2$, methoxyl, ethyoxyl or nitro.

2. The compounds of formula (A) or salts or solvates thereof or the solvates of salts thereof according to claim 1, wherein W represents dimethylamino, diethylamino, methylethylamino, methylallylamino, ethylallylamino, propylallyamino, diallylamino, ethanolamino or any one of the following formulas:

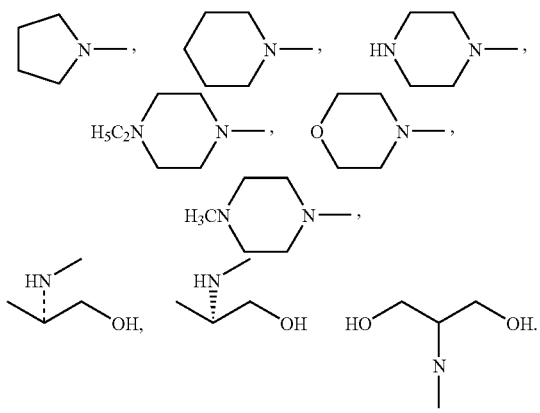

3. The compounds of formula (A) or salts or solvates thereof or the solvates of salts thereof according to claim 1, wherein Y represents H; W represents dimethylamino, diethylamino, methylethylamino, diallylamino or any one of the following formulas:

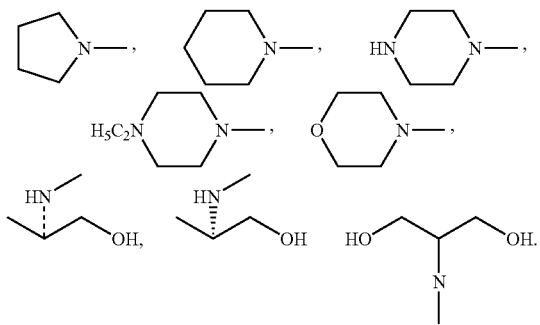

4. The compounds of formula (A) or salts or solvates thereof or the solvates of salts thereof according to claim 1, wherein Q represents any one of the following formulas:

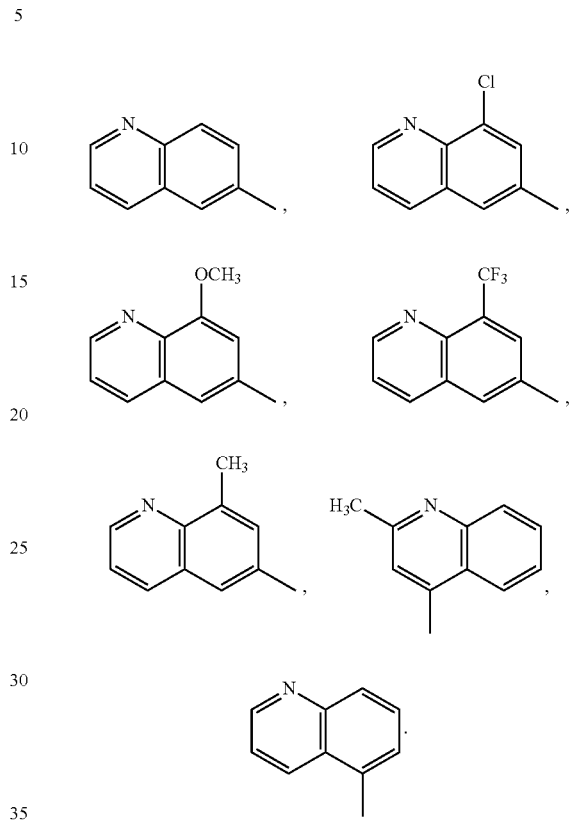

5. The compounds of formula (A) or salts or solvates thereof or the solvates of salts thereof according to claim 1, wherein the compound of formula (A) represents any one of the following compounds:

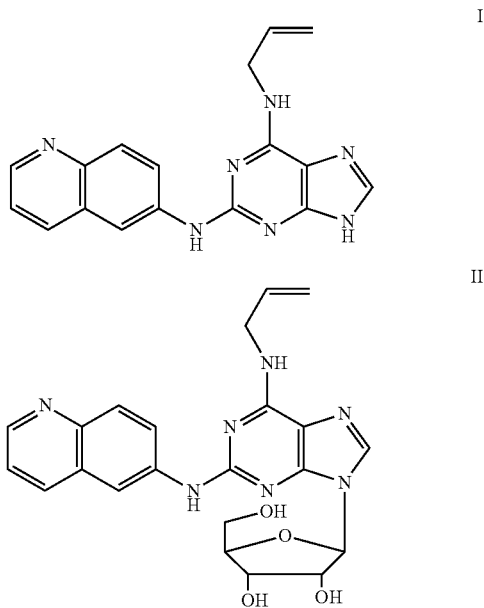

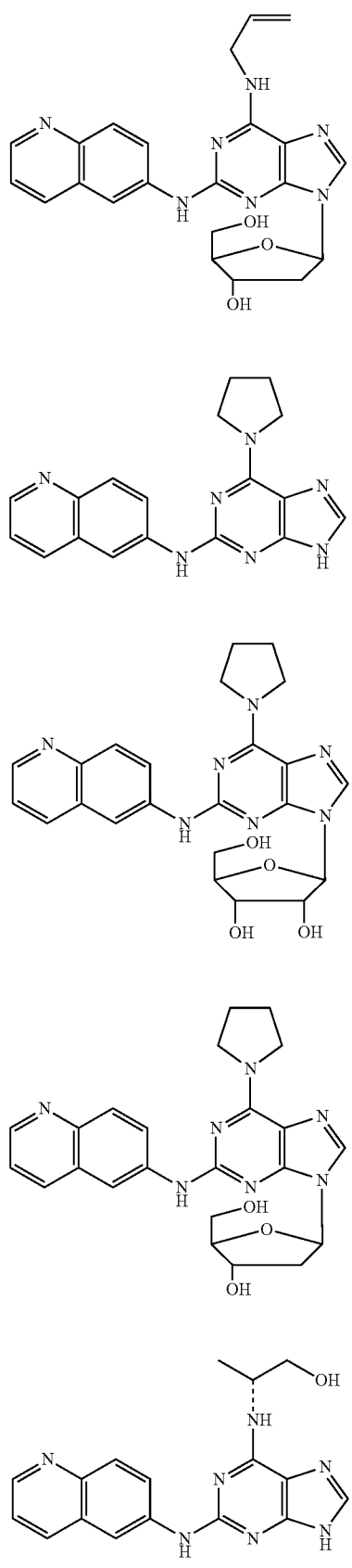
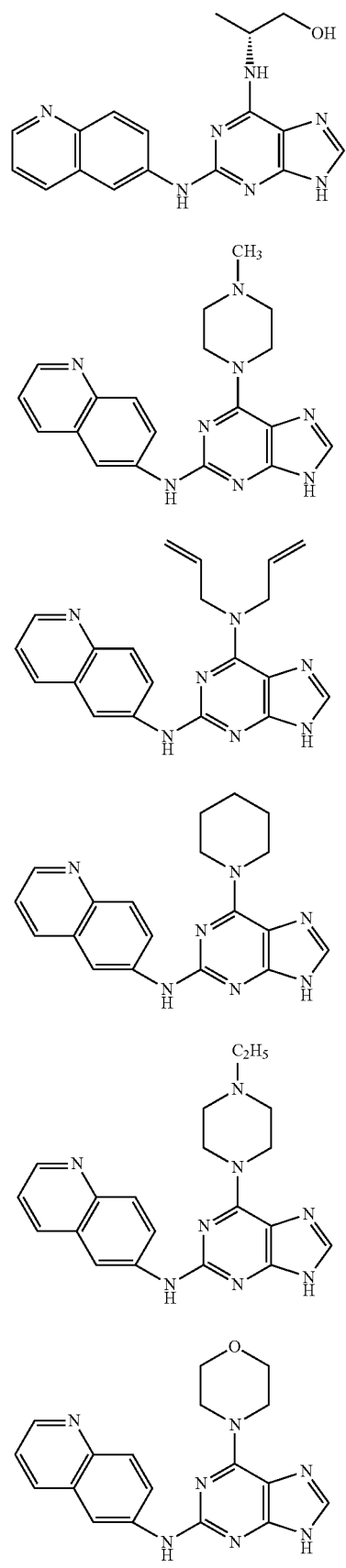

XVIII

XIX

XX

XXI

6. A pharmaceutical composition, wherein the pharmaceutical composition consists of the compounds of formula (A) or salts or solvates thereof or the solvates of salts thereof according to claim 1 and one or more pharmaceutical acceptable excipients.

7. A pharmaceutical composition, wherein the pharmaceutical composition consists of the compounds of formula (A) or salts or solvates thereof or the solvates of salts thereof according to claim 2 and one or more pharmaceutical acceptable excipients.

8. A pharmaceutical composition, wherein the pharmaceutical composition consists of the compounds of formula (A) or salts or solvates thereof or the solvates of salts thereof according to claim 3 and one or more pharmaceutical acceptable excipients.

9. A pharmaceutical composition, wherein the pharmaceutical composition consists of the compounds of formula (A) or salts or solvates thereof or the solvates of salts thereof according to claim 4 and one or more pharmaceutical acceptable excipients.

10. A pharmaceutical composition, wherein the pharmaceutical composition consists of the compounds of formula (A) or salts or solvates thereof or the solvates of salts thereof according to claim 5 and one or more pharmaceutical acceptable excipients.

11. The pharmaceutical composition according to claim 6, wherein the salt is acidic addition salts produced by organic acid or inorganic acid, or the salt is basic addition salts produced by organic base or inorganic base; the acid is hydrochloric acid, sulphuric acid, hydrobromic acid, methanesulfonic acid, benzene sulfonic acid, paratoluenesulfonic acid, maleic acid, fumaric acid, lactic acid, or citric acid.

12. The pharmaceutical composition according to claim 6, wherein the pharmaceutical composition is in the form of a tablet, a capsule, a pill, an oral liquid preparation, a granule, a powder, an injection, an implant or an external preparation.

13. A method for preparing the above compounds of formula (A) or salts or solvates thereof or the solvates of salts thereof, wherein the method includes the following steps:

1) firstly reacting the compound (a) with 2,3-dihydropyrane under catalysis of catalysts such as paratoluenesulfonic acid or pyridinium salt of paratoluenesulfonic acid; and then in the presence of depickling solvent such as triethylamine, sodium carbonate, potassium carbonate or sodium bicarbonate, condensating with W at a condensation reaction temperature of 20~100° C. to obtain compound (b);

2) in the presence of catalysts, bases and aprotic solvents, undergoing catalytic coupling reaction and deprotecting & salt-forming reaction of deprotecting group of compound (b) and Q-NH$_2$ at a catalytic coupling reaction temperature of 15~150° C., to obtain compound (d);

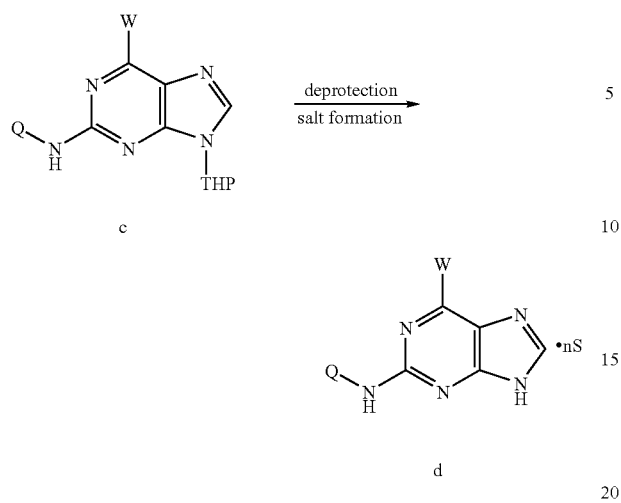
wherein, in the catalytic coupling reaction, the ligand includes tri-o-tolylphosphine, tri-tert-butylphosphine, 2,2'-diphenylphosphine-1,1'-binaphthalene, 1,1'-diphenylphosphine-ferrocene, bis(2-diphenylphosphinophenyl)ether, 9,9-dimethyl-4,5-diphenylphosphine xanthene, or the ligand is the compounds of formula 1, 2, 3, 4, 5, 6, 7, 8, 9, 10 or 11;
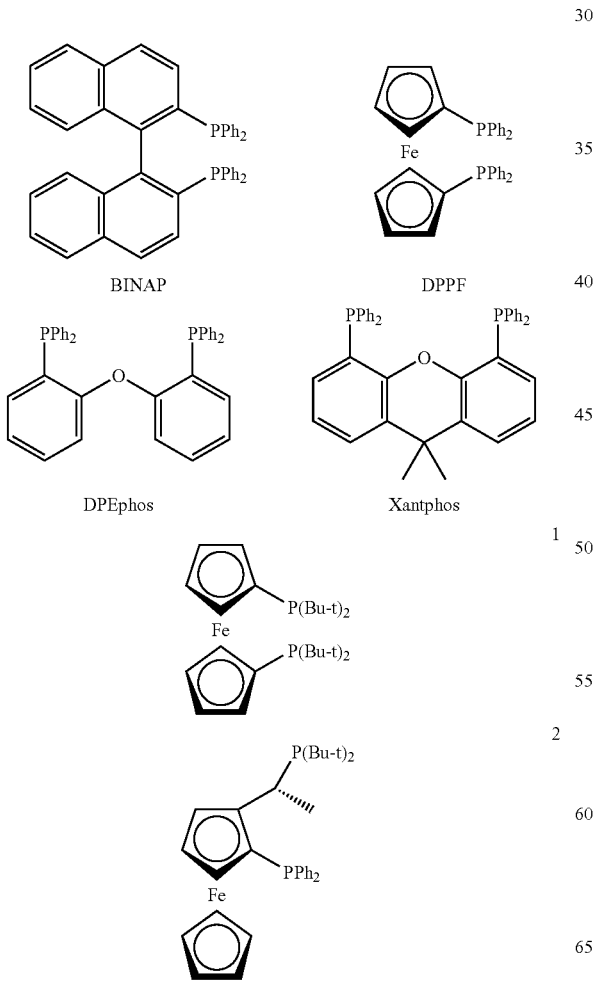
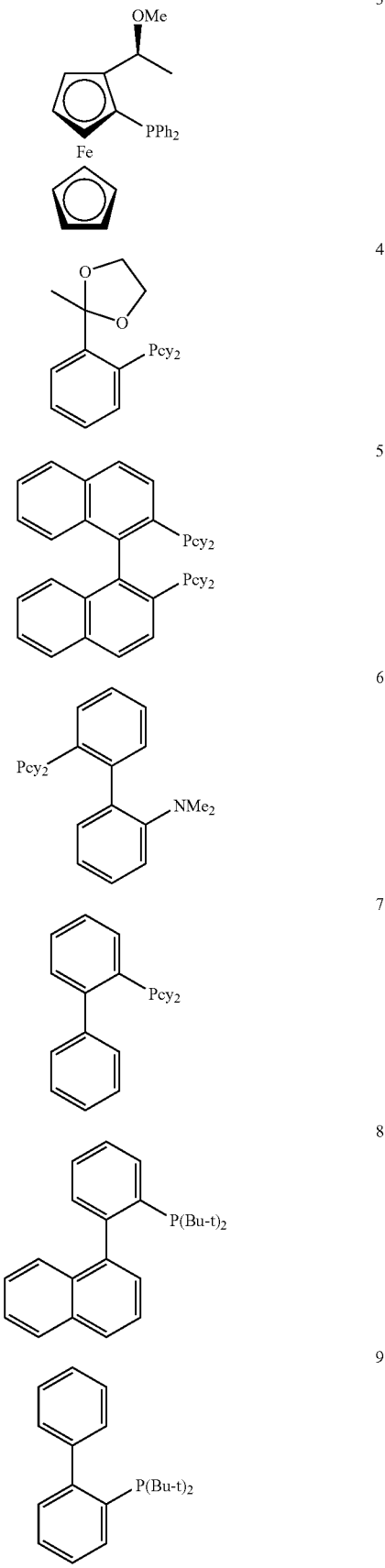

-continued

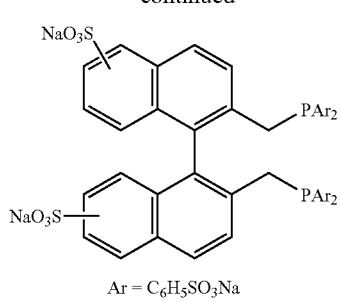

Ar = C₆H₅SO₃Na

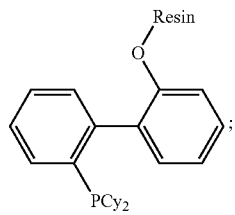

the catalyst is a transition metal catalyst of palladium or nickel such as PdCl₂, Pd(OAc)₂, Pd₂(dba)₃, Ni(OAc)₂ or Ni/C;

the base is sodium tert-butoxide, potassium tert-butoxide, potassium carbonate, cesium carbonate or tripotassium phosphate;

the deprotecting & salt-forming reaction could be carried out under the acidic condition such as hydrochloric acid, sulphuric acid, hydrobromic acid, methanesulfonic acid, benzene sulfonic acid, paratoluenesulfonic acid, maleic acid, fumaric acid, lactic acid or citric acid;

3) neutralizing compound (d) with sodium carbonate, potassium carbonate, sodium hydroxide, or potassium hydroxide to obtain compound (e),

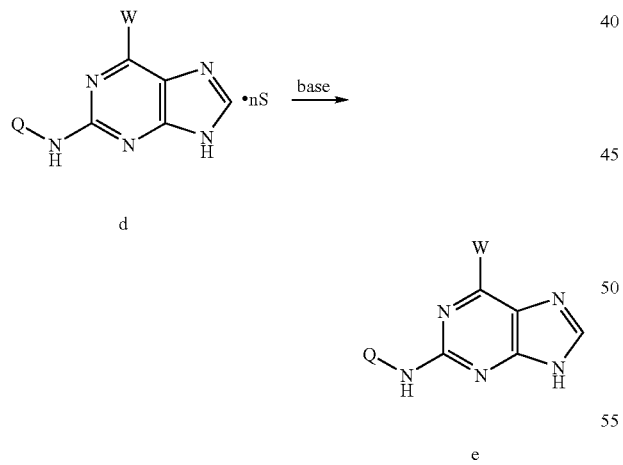

wherein:

W represents an optionally monosubstituted $C_3$~$C_6$ straight or branched alkenyl or alkynyl amino, an optionally disubstituted $C_1$~$C_6$ straight or branched alkylamino, an optionally disubstituted $C_3$~$C_6$ straight or branched alkenyl or alkynyl amino;

W may also represent amino substituted by two different $C_1$~$C_6$ straight or branched alkane, or represent amino substituted by two different $C_3$~$C_6$ straight or branched olefin, or amino which one end is substituted by $C_1$~$C_6$ alkane and the other end is substituted by $C_3$~$C_6$ olefin, or an optionally substituted heterocycle pyrrolidine, piperidine, morpholine or piperazidine;

the substituent represents $C_1$~$C_6$ straight or branched alkyl or halogen or hydroxyl;

Y represents H or a pharmaceutically acceptable saccharide, wherein the saccharide represents any one of the following formulas:

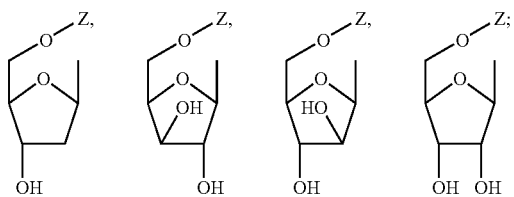

Z represents H or any one of the following formulas:

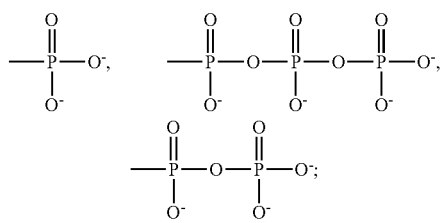

Q represents any one of the following formulas:

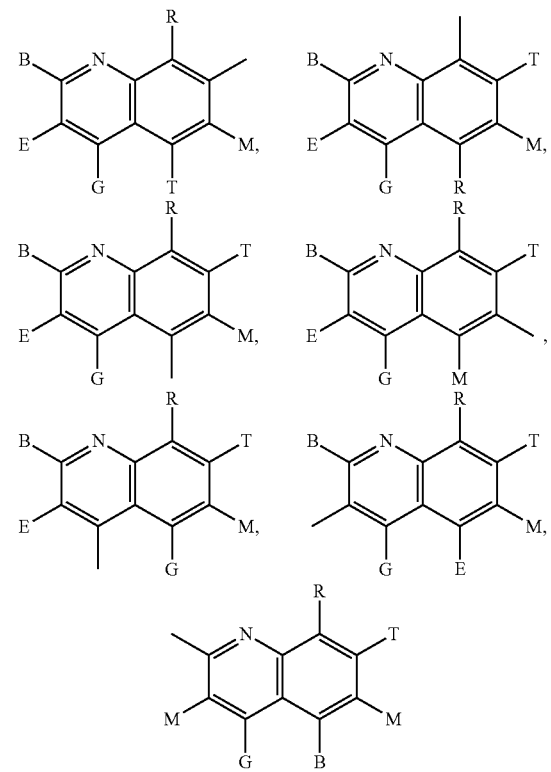

in the above formulas, B, E, G, R, T, M each independently represents a H or a $C_1$~$C_6$ straight or branched alkyl, or haloalkyl, a $C_3$~$C_6$ cycloalkyl, halogen, CN, $NH_2$, methoxyl, ethyoxyl or nitro

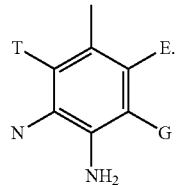

14. A method for preparing the above compounds of formula (A) or salts or solvates thereof or the solvates of salts thereof according to claim 13, wherein the reacting molar ratio of compound (a) to 2,3-dihydropyrane is about 1:1~5, the molar ratio of compound (a) to W is about 1:1~5, the condensation reaction temperature is about 40~60° C.

15. A method for preparing the above compounds of formula (A) or salts or solvates thereof or the solvates of salts thereof according to claim 13, wherein the molar ratio of compound (b) to Q-$NH_2$ is about 1:0.5~2; the catalytic coupling reaction temperature is about 55~120° C. or the reaction is carried out by using microwave heating; the aprotic solvent is tetrahydrofuran, isopropyl ether, ethylene glycol dimethyl ether, dioxane, pyridine, 1-methyl-2-pyrrolidone (NMP), 1,3-dimethyltrimethylene urea (DMPU), toluene or xylene or mixed solvents comprising one or more selected from the above-mentioned solvents.

16. A method for preparing the above compounds of formula (A) or salts or solvates thereof or the solvates of salts thereof according to claim 13, wherein in the deprotecting & salt-forming reaction, the molar ratio of compound (c) to hydrochloric acid, sulphuric acid, hydrobromic acid, methanesulfonic acid, benzene sulfonic acid, paratoluenesulfonic acid, maleic acid, fumaric acid, lactic acid or citric acid is respectively about 1:1~10.

17. A method of treatment or prophylaxis of tumor diseases comprising administering a pharmaceutical composition comprising a compound of Formula (A) or salts or solvates thereof or the solvates of salts thereof according to claim 11.

18. The method according to claim 17, wherein the tumor diseases include one or more of lung cancer, liver cancer, leukemia, osteocarcinoma, pancreas cancer, skin cancer, melanoma, metrocarcinoma, oophoroma, rectal carcinoma, gastric carcinoma, colon cancer, breast carcinoma, salpingo carcinoma, endometrium carcinoma, cervix carcinoma, vagina carcinoma, carcinoma of vulva, esophagus carcinoma, small intestine carcinoma, endocrinium carcinoma, soft tissue sarcoma, urethra carcinoma, prostatic cancer, lymphocytoma, bladder cancer, kidney or ureter cancer, tumors of vertebral column, tumors in the neuroglia of the brain, and pituitary adenoma.

* * * * *